United States Patent
Whitfield et al.

(10) Patent No.: US 12,137,908 B2
(45) Date of Patent: Nov. 12, 2024

(54) ANVIL BUTTRESS LOADING SYSTEM FOR SURGICAL STAPLING APPARATUS

(71) Applicant: Covidien LP, Mansfield, MA (US)

(72) Inventors: Kenneth H. Whitfield, North Haven, CT (US); Roanit A. Fernandes, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/386,657

(22) Filed: Nov. 3, 2023

(65) Prior Publication Data

US 2024/0058003 A1 Feb. 22, 2024

Related U.S. Application Data

(63) Continuation of application No. 17/533,745, filed on Nov. 23, 2021, now Pat. No. 11,806,017.

(51) Int. Cl.
*A61B 17/072* (2006.01)
*A61B 17/00* (2006.01)

(52) U.S. Cl.
CPC ...... *A61B 17/07292* (2013.01); *A61B 2017/0053* (2013.01); *A61B 2017/07257* (2013.01)

(58) Field of Classification Search
CPC ........ A61B 17/07292; A61B 17/07207; A61B 2017/0053; A61B 2017/07257
See application file for complete search history.

(56) References Cited

U.S. PATENT DOCUMENTS

| | | | |
|---|---|---|---|
| 3,054,406 | A | 9/1962 | Usher |
| 3,124,136 | A | 3/1964 | Usher |
| 3,364,200 | A | 1/1968 | Ashton et al. |
| 3,499,591 | A | 3/1970 | Green |
| 3,797,494 | A | 3/1974 | Zaffaroni |
| 3,939,068 | A | 2/1976 | Wendt et al. |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

Extended European Search Report corresponding to EP 14 16 9739.1, completed Aug. 19, 2014 and Aug. 29, 2014; (7 pp).

(Continued)

*Primary Examiner* — Nathaniel C Chukwurah

(57) ABSTRACT

A surgical buttress loading system includes an anvil having a spring assembly biased against a tissue facing surface of an anvil body and a loading tool including a cavity configured to receive the anvil therein, a buttress cartridge including a surgical buttress releasably disposed thereon, an actuator, and a handle operably coupled to the buttress cartridge. When the anvil is positioned within the cavity of the loading tool and the handle is moved to from an unactuated position to an actuated position, the handle moves the actuator to from a retracted position to an extended position and into engagement with the spring assembly of the anvil to lift the spring assembly off of the tissue facing surface and then slides the buttress cartridge towards the spring assembly to move a proximal end portion of the surgical buttress between the spring assembly and the tissue facing surface.

17 Claims, 20 Drawing Sheets

(56) References Cited

U.S. PATENT DOCUMENTS

| | | |
|---|---|---|
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,473,077 A | 9/1984 | Noiles et al. |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |

(56) References Cited

U.S. PATENT DOCUMENTS

| | | |
|---|---|---|
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |

(56) References Cited

U.S. PATENT DOCUMENTS

| | | |
|---|---|---|
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,828,023 B2 | 9/2014 | Neff et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommersberger) et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (Prommersberger) Stopek |
| 10,098,639 B2 | 10/2018 | Hodgkinson |
| 10,111,659 B2 | 10/2018 | Racenet et al. |
| 10,154,840 B2 | 12/2018 | Viola et al. |
| 10,349,940 B2 | 7/2019 | Zeiner et al. |
| 10,426,468 B2 | 10/2019 | Contini et al. |
| 11,806,017 B2 | 11/2023 | Whitfield et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | De La Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |

(56) References Cited

U.S. PATENT DOCUMENTS

| | | |
|---|---|---|
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0201938 A1 | 7/2015 | Swayze et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0119391 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson, Ph.D et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168628 A1* | 6/2018 | Hunter ............... A61B 17/0682 |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0235617 A1 | 8/2018 | Shelton, IV et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |
| 2019/0192158 A1* | 6/2019 | Scott ............... A61B 17/07207 |
| 2020/0205822 A1 | 7/2020 | Heupel et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 9516221 A1 | 6/1995 |
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 14 15 7997.9, completed Sep. 9, 2014 and dated Sep. 17, 2014; (8 pp).

Extended European Search Report corresponding to EP 14 16 8904.2, completed Sep. 10, 2014 and dated Sep. 18, 2014; (8 pp).

Extended European Search Report corresponding to EP 13 19 4995.0, completed Jun. 5, 2014 and dated Oct. 13, 2014; (10 pp).

Extended European Search Report corresponding to EP 13 15 4571.7, completed Oct. 10, 2014 and dated Oct. 2014; (8 pp).

Extended European Search Report corresponding to EP 14 18 1125.7, completed Oct. 16, 2014 and dated Oct. 24, 2014; (7 pp).

Extended European Search Report corresponding to EP 14 18 1127.3, completed Oct. 16, 2014 and dated Nov. 10, 2014; (8 pp).

Extended European Search Report corresponding to EP 14 19 0419.3, completed Mar. 24, 2015 and dated Mar. 30, 2015; (6 pp).

European Office Action corresponding to EP 12 198 776.2 dated Apr. 7, 2015.

European Office Action corresponding to EP 13 156 297.7 dated Apr. 10, 2015.

Australian Examination Report No. 1 corresponding to AU 2011250822 dated May 18, 2015.

European Office Action corresponding to EP 12 186 175.1 dated Jun. 1, 2015.

Chinese Office Action corresponding to CN 201010517292.8 dated Jun. 2, 2015.

Extended European Search Report corresponding to EP 14 17 4814.5 dated Jun. 9, 2015.

Australian Examination Report No. 1 corresponding to AU 2014200584 dated Jun. 15, 2015.

European Office Action corresponding to EP 13 180 881.8 dated Jun. 19, 2015.

European Office Action corresponding to EP 14 157 195.0 dated Jul. 2, 2015.

Extended European Search Report corresponding to EP 12 19 6902.6 dated Aug. 6, 2015.

Extended European Search Report corresponding to EP 14 15 2060.1 dated Aug. 14, 2015.

Chinese Office Action corresponding to CN 201210129787.2 dated Aug. 24, 2015.

(56) References Cited

OTHER PUBLICATIONS

Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686, 105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Office Action corresponding to EP 14 17 2681.0 dated May 13, 2016.
U.S. Appl. No. 17/533,745, filed Nov. 23, 2021, Patented, U.S. Pat. No. 11,806,017.
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 182911. 1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.

(56) References Cited

OTHER PUBLICATIONS

Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
International Search Report and Written Opinion issued in corresponding International Application No. PCT/B2022/060725 dated Feb. 6, 2023, 12 pages.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.

(56) References Cited

OTHER PUBLICATIONS

Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Australian Examination Report No. 1 corresponding to AU 2014200793 dated Sep. 2, 2017.

* cited by examiner

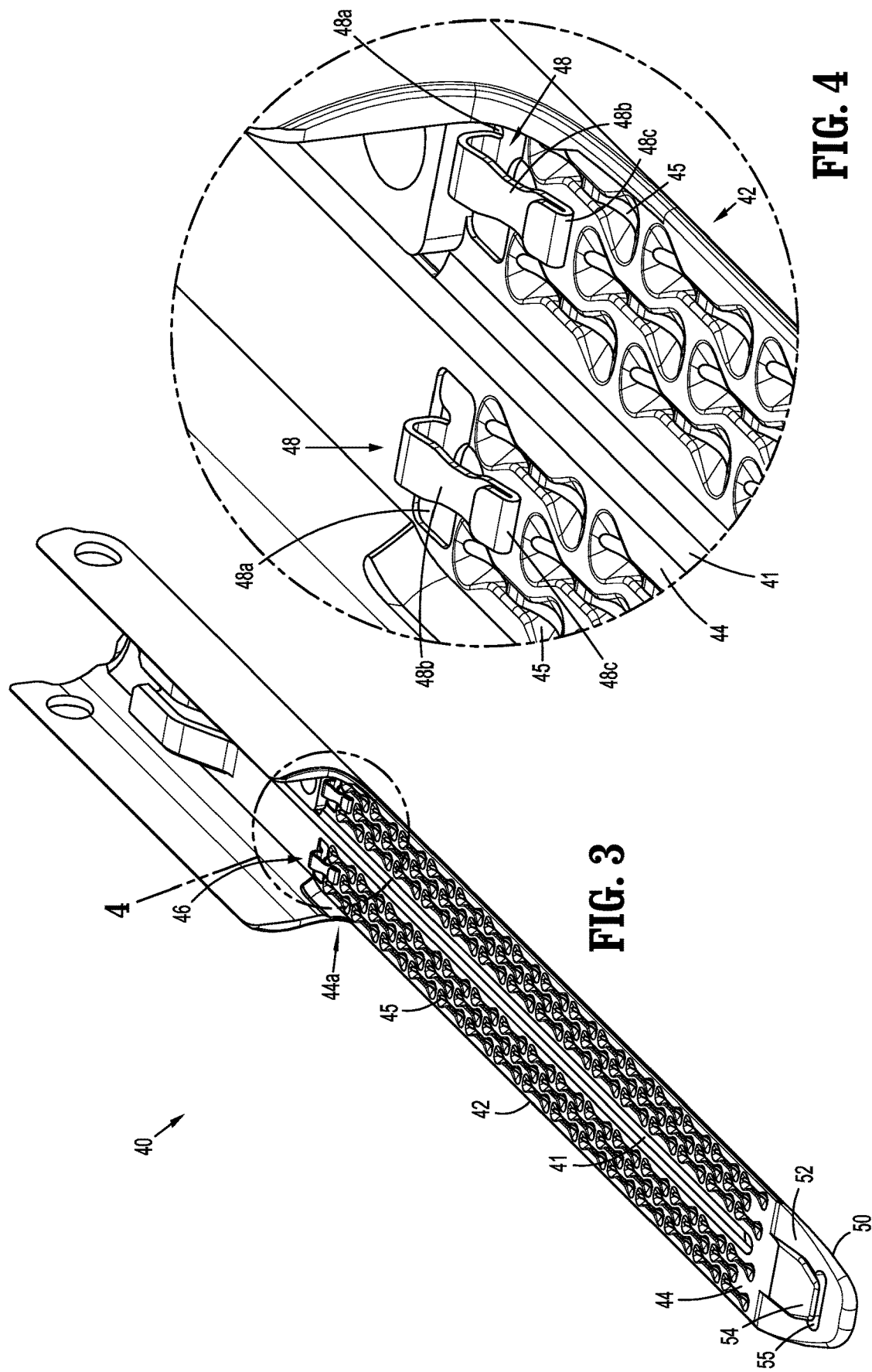

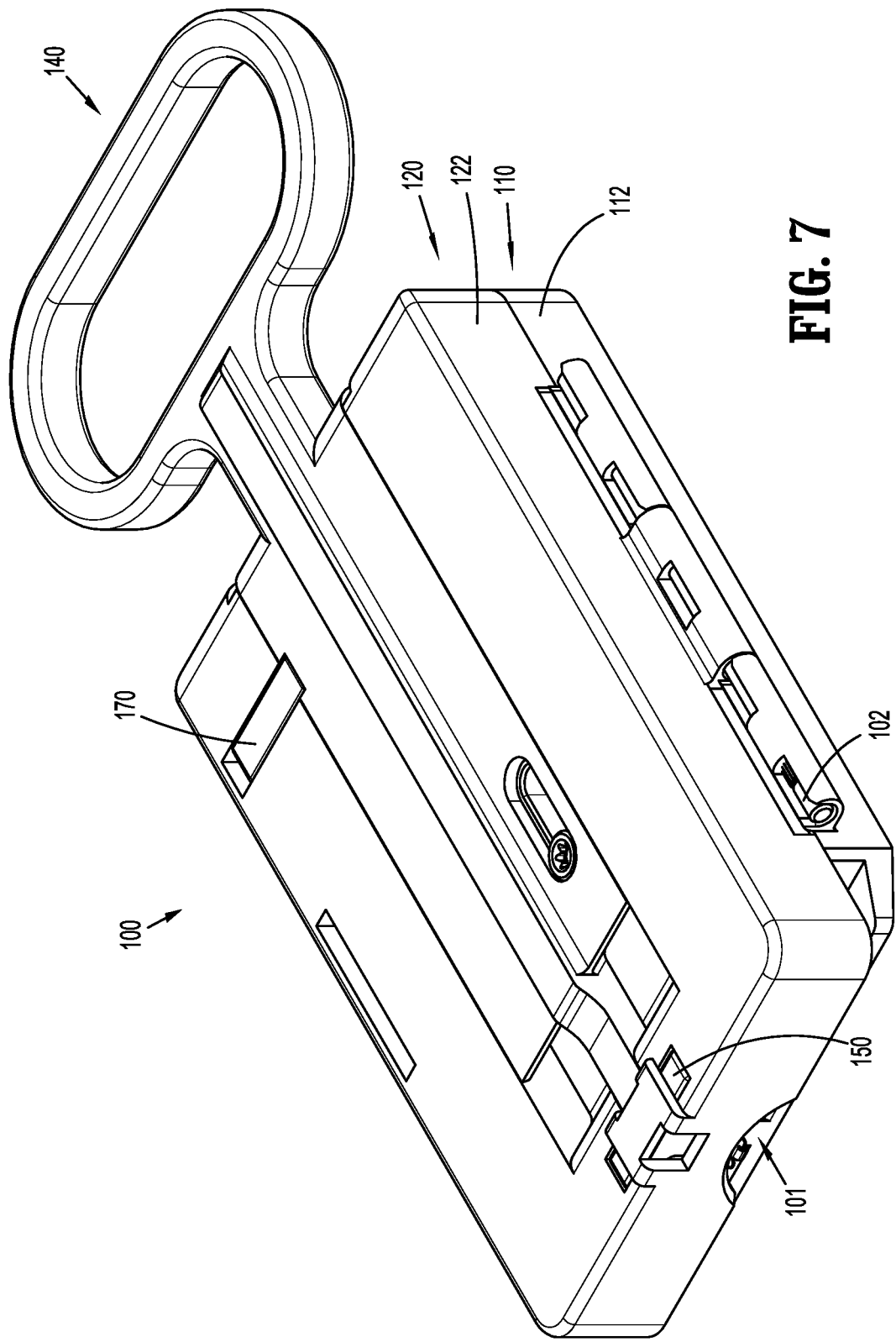

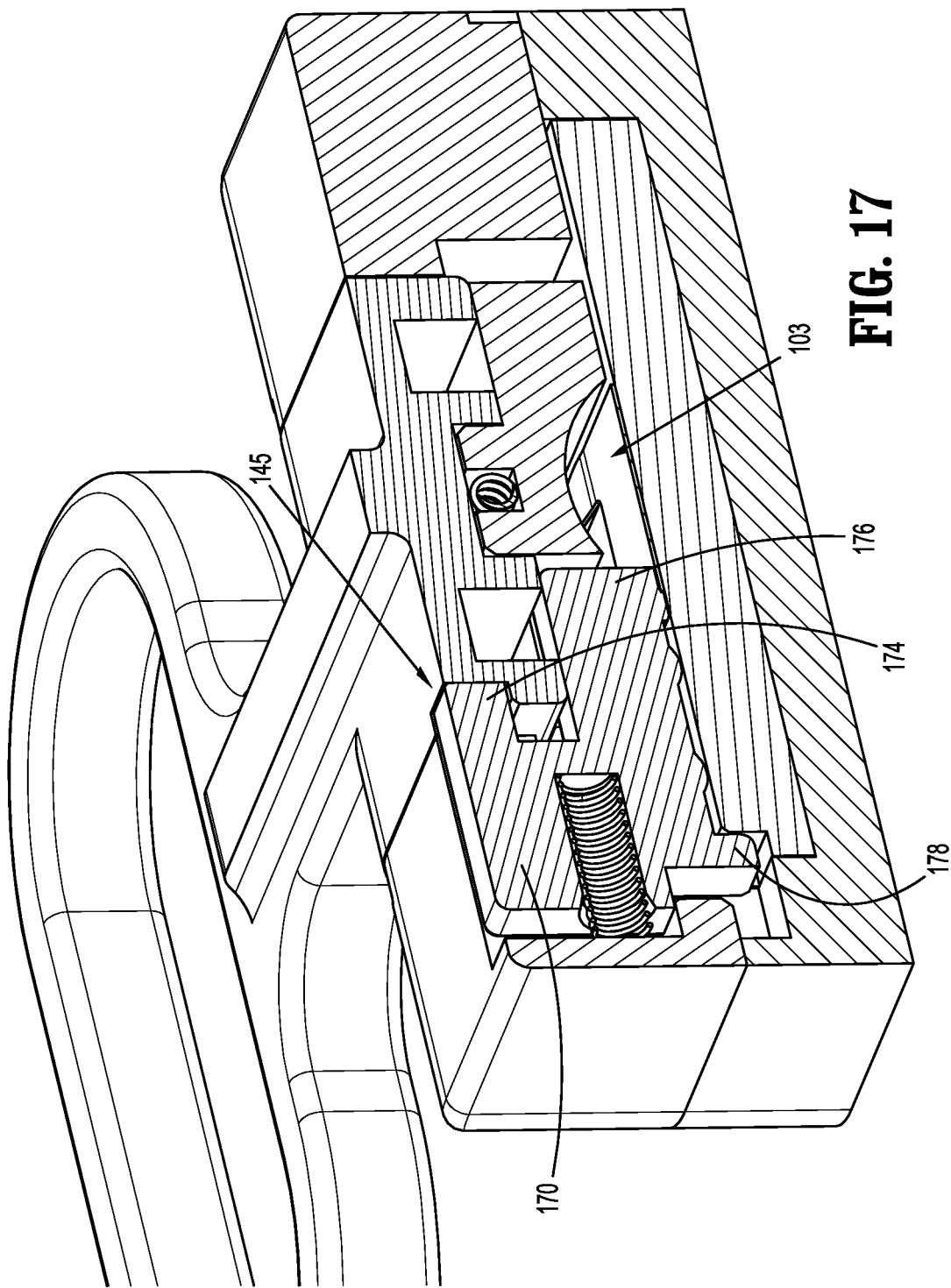

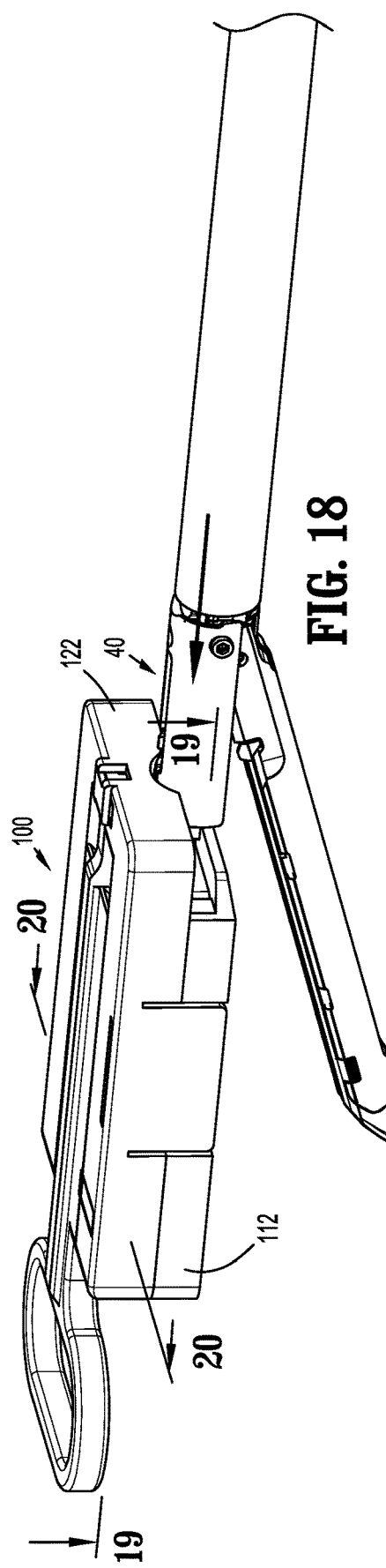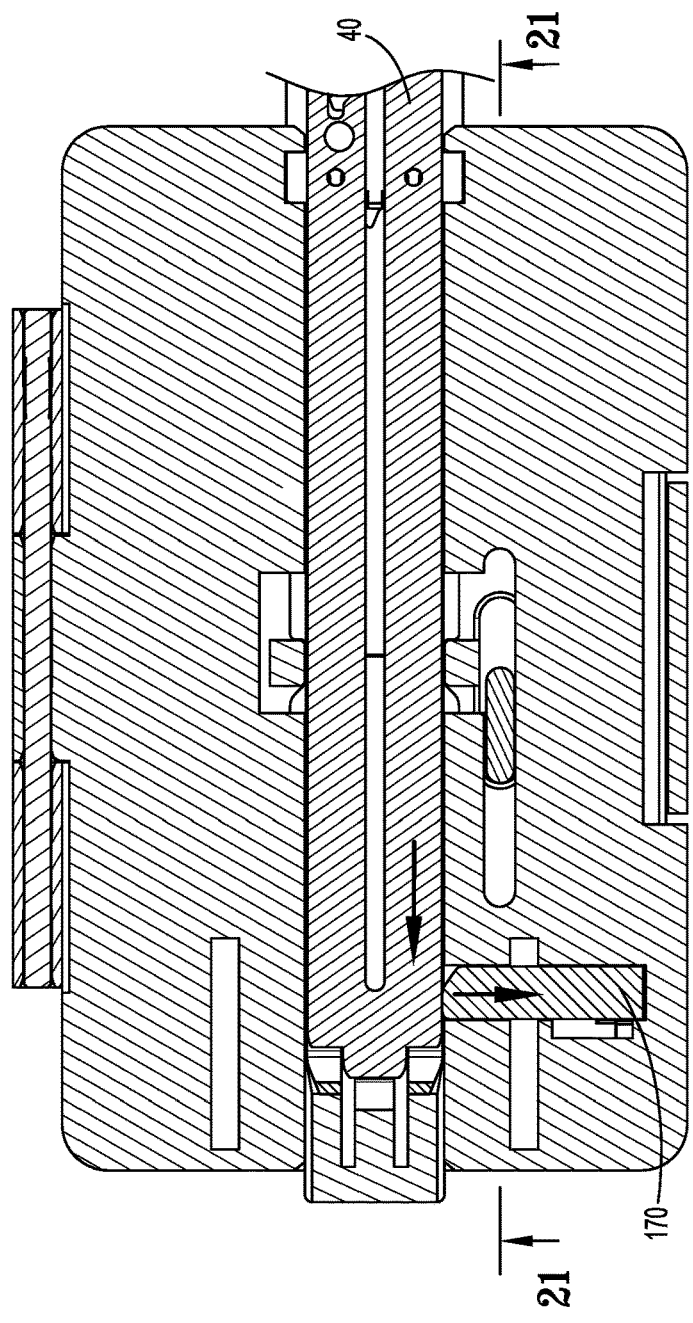

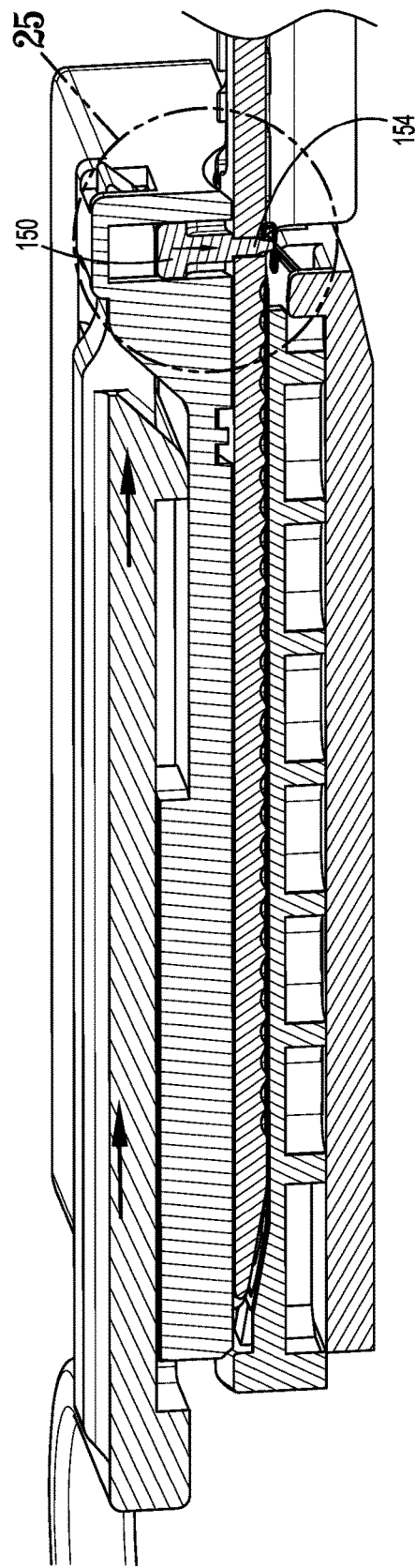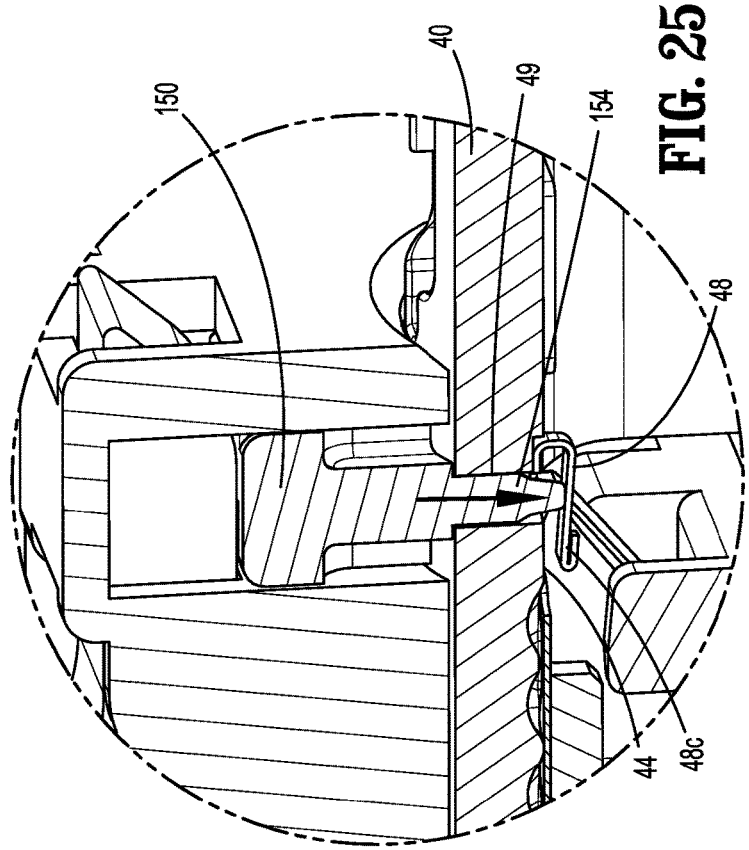

ANVIL BUTTRESS LOADING SYSTEM FOR SURGICAL STAPLING APPARATUS

CROSS-REFERENCE TO RELATED APPLICATIONS

This application is a Continuation Application which claims the benefit of and priority to U.S. patent application Ser. No. 17/533,745, filed Nov. 23, 2021 (now U.S. Pat. No. 11,806,017), the disclosure of which is hereby incorporated by reference in its entirety.

FIELD

This application generally relates to surgical stapling apparatus, and more particularly, to surgical buttress loading tools for releasably securing surgical buttresses to anvil assemblies of the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon. The buttress material reinforces the staple or suture line as well as covers the juncture of the tissues to reduce leakage prior to healing.

SUMMARY

This disclosure relates to anvil side (single-sided) buttress attachment onto a loading unit of a surgical stapling apparatus. The surgical buttress loading tools of this disclosure are designed to make surgical buttress attachment (e.g., in the operating room) a simple, straightforward, and cost-effective procedure.

In one aspect, the disclosure provides a surgical buttress loading system including an anvil and a surgical buttress loading tool. The anvil includes an anvil body including a spring assembly biased against a tissue facing surface of the anvil body. The surgical buttress loading tool includes a first housing portion, a second housing portion, a buttress cartridge, an actuator, and a handle. The first and second housing portions define a cavity therebetween that is configured to receive the anvil therein. The buttress cartridge is supported on the first housing portion and includes a surgical buttress releasably disposed thereon. The actuator is disposed within a proximal end portion of the second housing portion and is movable between retracted and extended positions. The handle is supported on the second housing portion and is operably coupled to the buttress cartridge. The handle is slidable between unactuated and actuated positions. When the anvil is positioned within the cavity of the surgical buttress loading tool and the handle is moved from the unactuated position to the actuated position, the handle moves the actuator from the retracted position to the extended position and into engagement with the spring assembly of the anvil to lift the spring assembly off of the tissue facing surface and then slides the buttress cartridge towards the spring assembly to move a proximal end portion of the surgical buttress between the spring assembly and the tissue facing surface. When the handle is moved back to the unactuated position, the actuator moves back to the retracted position and disengages from the spring assembly to releasably secure the proximal end portion of the surgical buttress to the anvil.

The spring assembly may include springs that each includes an arm extending over a through-hole defined in the anvil, and the actuator may include pins aligned with the through-holes when the anvil is positioned within the cavity of the surgical buttress loading tool. When the actuator is moved to the extended position, the pins of the actuator may extend through the though-holes and push the arms of the springs away from the tissue facing surface of the anvil plate.

In aspects, the anvil includes an anvil tip extending distally from the anvil body. The anvil tip may include a hook and when the handle is moved to the actuated position, the buttress cartridge may slide a distal end portion of the surgical buttress over the hook to releasably secure the distal end portion of the surgical buttress to the anvil. In some aspects, the distal end portion of the surgical buttress includes a window defined therein, and the hook extends through the window.

The handle may include a tab extending into an elongated slot of the buttress cartridge, and when the handle is moved to the actuated position, the tab may initially move within the elongated slot while the handle moves the actuator to the extended position before sliding the buttress cartridge. The handle may include a sloped proximal end positioned adjacent to a ramped surface of the actuator and when the handle is moved to the actuated position, the sloped proximal end may cam against the ramped surface.

In aspects, the surgical buttress loading tool includes an applicator spring secured to the second housing portion. The applicator spring includes a spring leg biasing the actuator in the retracted position. In some aspects, the applicator spring includes a spring arm holding the surgical buttress against the buttress cartridge until the anvil is positioned into the cavity of the surgical buttress loading tool.

The surgical buttress loading tool may include an interlock disposed within the second housing portion. The interlock may be configured to lock the handle from movement until the anvil is positioned within the cavity of the surgical buttress loading tool. In aspects, the interlock is laterally movable between a locked position and an unlocked position and when the interlock is in the locked position, a first arm of the interlock is engaged with a notch defined in the handle to prevent movement of the handle between the unactuated and actuated positions. In some aspects, the interlock includes a second arm extending partially into the cavity defined between the first and second housing portions and, when the anvil is inserted into the cavity, the anvil moves the interlock from the locked position to the unlocked position. In certain aspects, the interlock includes a leg and when the interlock is in the locked position, the leg is engaged with a notch defined in the buttress cartridge to prevent movement of the buttress cartridge.

In another aspect, the disclosure provides a method of loading a surgical buttress onto an anvil including: inserting an anvil into a cavity of a surgical buttress loading tool, the anvil including an anvil body including a spring assembly biased against a tissue facing surface of the anvil body and the anvil buttress loading tool including first and second housing portions defining the cavity therebetween, a buttress cartridge supported on the first housing portion and including a surgical buttress releasably disposed thereon, an actuator disposed within a proximal end portion of the second housing portion, the actuator movable between retracted and extended positions, and a handle supported on the second housing portion and operably coupled to the buttress cartridge, the handle slidable between unactuated and actuated positions; moving the handle from the unactuated position to the actuated position so that the handle moves the actuator from the retracted position to the extended position and into engagement with the spring assembly of the anvil to lift the spring assembly off of the tissue facing surface and then slides the buttress cartridge towards the spring assembly to move a proximal end portion of the surgical buttress between the spring assembly and the tissue facing surface; and moving the handle back to the unactuated position so that the actuator moves back to the retracted position and disengages from the spring assembly to releasably secure the proximal end portion of the surgical buttress to the anvil.

According to yet another aspect of the disclosure, a surgical buttress loading tool for use with an anvil including an anvil body having a spring assembly biased against a tissue facing surface of the anvil body, is provided. The surgical buttress loading tool includes first and second housing portions defining a cavity therebetween, the cavity configured to receive the anvil therein; a buttress cartridge supported on the first housing portion and including a surgical buttress releasably disposed thereon; an actuator disposed within a proximal end portion of the second housing portion, the actuator movable between retracted and extended positions; and a handle supported on the second housing portion and operably coupled to the buttress cartridge, the handle slidable between unactuated and actuated positions.

In use, when the anvil is positioned within the cavity of the surgical buttress loading tool and the handle is moved from the unactuated position to the actuated position, the handle moves the actuator from the retracted position to the extended position and into engagement with the spring assembly of the anvil to lift the spring assembly off of the tissue facing surface and then slides the buttress cartridge towards the spring assembly to move a proximal end portion of the surgical buttress between the spring assembly and the tissue facing surface. Further, when the handle is moved back to the unactuated position, the actuator moves back to the retracted position and disengages from the spring assembly to releasably secure the proximal end portion of the surgical buttress to the anvil.

The handle may include a tab extending into an elongated slot of the buttress cartridge. In use, when the handle is moved to the actuated position, the tab may initially move within the elongated slot while the handle moves the actuator to the extended position before sliding the buttress cartridge.

The handle may include a sloped proximal end positioned adjacent to a ramped surface of the actuator. In use, when the handle is moved to the actuated position, the sloped proximal end may cam against the ramped surface.

The surgical buttress loading tool may further include an applicator spring secured to the second housing portion. The applicator spring may include a spring leg biasing the actuator in the retracted position.

The applicator spring may include a spring arm holding the surgical buttress against the buttress cartridge until the anvil is positioned into the cavity of the surgical buttress loading tool.

The surgical buttress loading tool may further include an interlock disposed within the second housing portion. The interlock may be configured to lock the handle from movement until the anvil is positioned within the cavity of the surgical buttress loading tool.

The interlock may be laterally movable between a locked position and an unlocked position and when the interlock is in the locked position, a first arm of the interlock is engaged with a notch defined in the handle to prevent movement of the handle between the unactuated and actuated positions.

The details of one or more aspects of the disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of the disclosure are described hereinbelow with reference to the drawings, which are incorporated in and constitute a part of this specification, wherein:

FIG. 3 is a perspective view of an anvil of the tool assembly of FIG. 2;

FIG. 4 is a close-up view of area of detail 4 in FIG. 3, illustrating a spring assembly of the anvil;

FIG. 7 is a perspective view of a loading tool, shown in a closed position, in accordance with aspects of the disclosure;

FIG. 17 is a cross-sectional view of loading tool of FIG. 13, taken along section line 17-17 of FIG. 13;

FIG. 18 is a perspective view of the loading tool of FIG. 13, shown with the anvil of FIG. 2 positioned within the loading tool;

FIG. 19 is a cross-sectional view of the loading tool and the anvil of FIG. 18, taken along section line 19-19 of FIG. 18;

FIG. 24 is a cross-sectional view of the loading tool and the anvil of FIG. 22, taken along section line 24-24 of FIG. 22;

FIG. 25 is a close-up view of the area of detail 25 indicated in FIG. 24;

DETAILED DESCRIPTION

Figure 1:
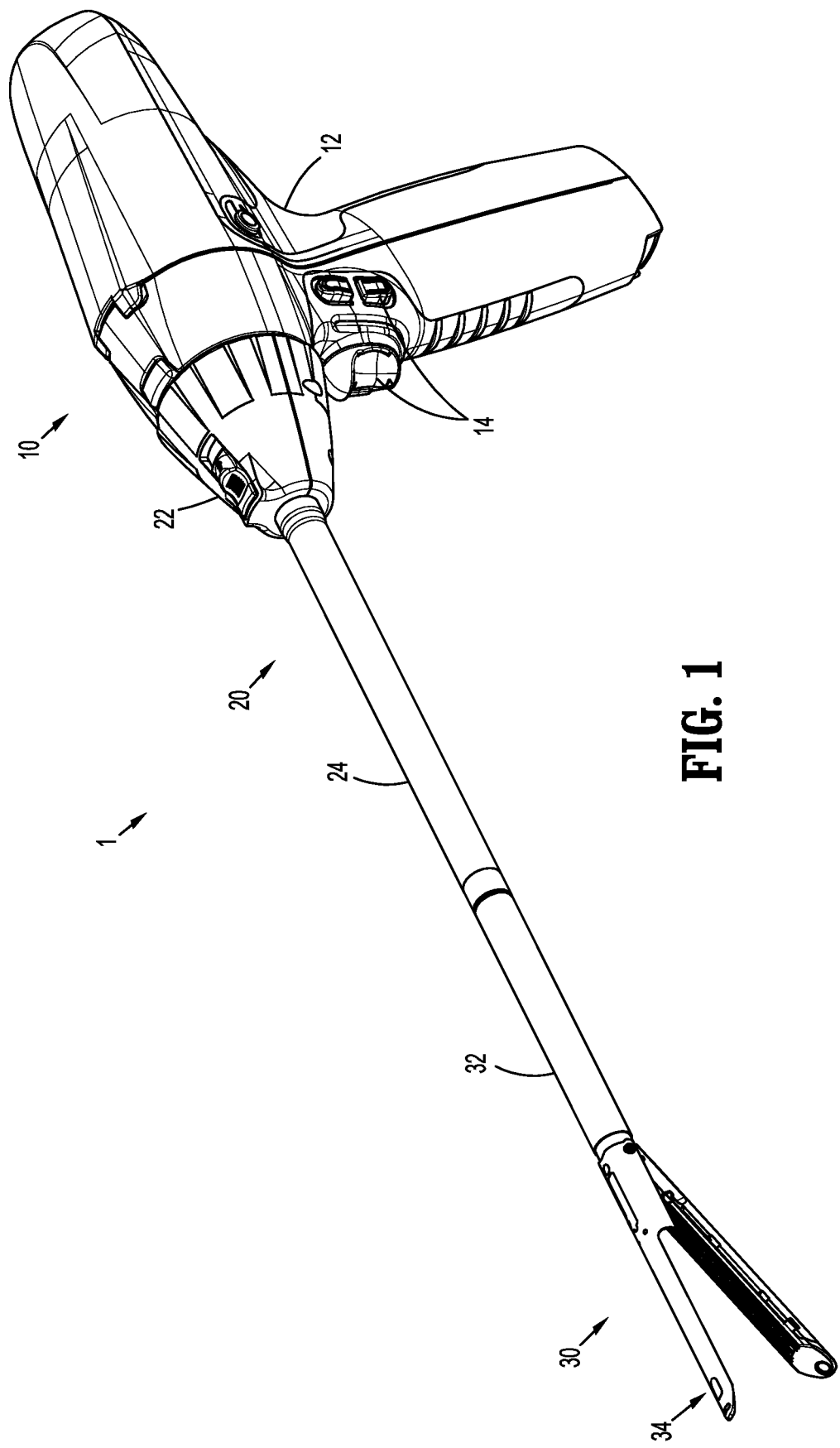
FIG. 1 is a perspective view of a surgical stapling apparatus in accordance with an aspect of the disclosure.

Aspects of the disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "downwardly," "upwardly," and the like, are used to ease description of aspects of this disclosure and are not intended to have any limiting effect on the ultimate orientation of a structure or any part thereof.

Referring now to FIG. 1, an exemplary surgical device or surgical stapling apparatus 1 is shown for use in stapling tissue in accordance with aspects of the disclosure. The surgical stapling apparatus 1 generally includes a handle assembly 10, an adapter assembly 20 extending distally from the handle assembly 10, and a loading unit 30 extending distally from the adapter assembly 20.

The surgical stapling apparatus 1 will further be described to the extent necessary to disclose aspects of the disclosure. For a detailed description of the structure and function of exemplary surgical devices, reference may be made to U.S. Pat. No. 10,426,468, the entire contents of which are incorporated herein by reference.

The handle assembly 10 includes a handle housing 12 housing a power-pack (not shown) configured to power and control various operations of the surgical stapling apparatus 1, and a plurality of actuators 14 (e.g., finger-actuated control buttons, knobs, toggles, slides, interfaces, and the like) for activating various functions of the surgical stapling apparatus 1. The adapter assembly 20 includes a knob housing 22 configured for operable connection to the handle assembly 10 and an elongate tubular body 24 configured for operable connection to the loading unit 30. Alternatively, the elongate tubular body 24 may be supported directly on the handle assembly 10 (e.g., permanently affixed to or integrally formed with the handle assembly).

Figure 2:
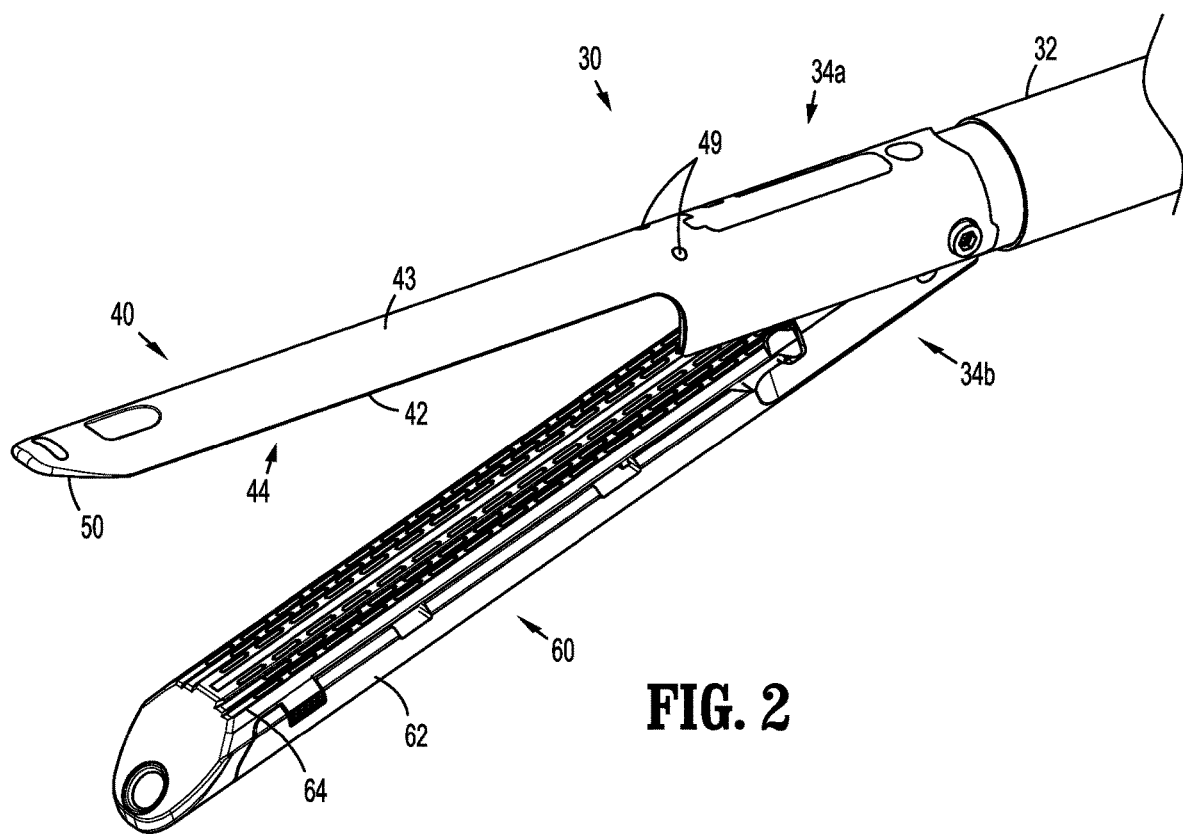
FIG. 2 is perspective view of a tool assembly of the surgical stapling apparatus of FIG. 1.

The loading unit 30 is a disposable loading unit ("DLU") that is releasably secured to the elongated tubular body 24 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly (e.g., a staple cartridge 64 as seen in FIG. 2) of the MULU is replaced after each staple and cut operation of the surgical stapling apparatus 1 a predetermined number of times before the entire MULU needs to be replaced. Alternatively, the loading unit 30 may be permanently affixed to the elongated tubular body 24.

As shown in FIGS. 1 and 2, the loading unit 30 includes a housing portion 32 and a tool or jaw assembly 34 including first and second jaw members 34a, 34b. The first jaw member 34a and/or the second jaw members 34b is pivotable with respect to the housing portion 32 such that the tool assembly 34 is movable between an open position in which the first and second jaw members 34a, 34b are spaced apart with respect to each other, and a closed position in which the first and second jaw members 34a, 34b are substantially adjacent each other. The first jaw member 34a of the tool assembly 34 includes an anvil assembly 40 (also referred to herein generally as an anvil) and the second jaw member 34b of the tool assembly 34 includes a staple cartridge assembly 60.

As shown in FIGS. 2 and 3, the anvil assembly 40 includes an anvil body 42 and an anvil tip 50 extending distally from the anvil body 42. The anvil body 42 has an outer surface 43 and an inner or tissue facing surface 44. The tissue facing surface 44 includes a central longitudinal slot 41 and staple forming pockets or cavities 45 defined therein. The central longitudinal slot 41 is configured for passage of a knife blade (not shown) therethrough during actuation of the surgical stapling apparatus 1 (FIG. 1). The staple forming pockets 45 are disposed in rows on opposed sides of the central longitudinal slot 41 and are configured to form staples (not shown) which are fired out of the staple cartridge assembly 60 during actuation of the surgical stapling apparatus 1 (FIG. 1). The anvil body 42 also includes a spring assembly 46 disposed at a proximal portion 44a of the tissue facing surface 44.

Figure 5:
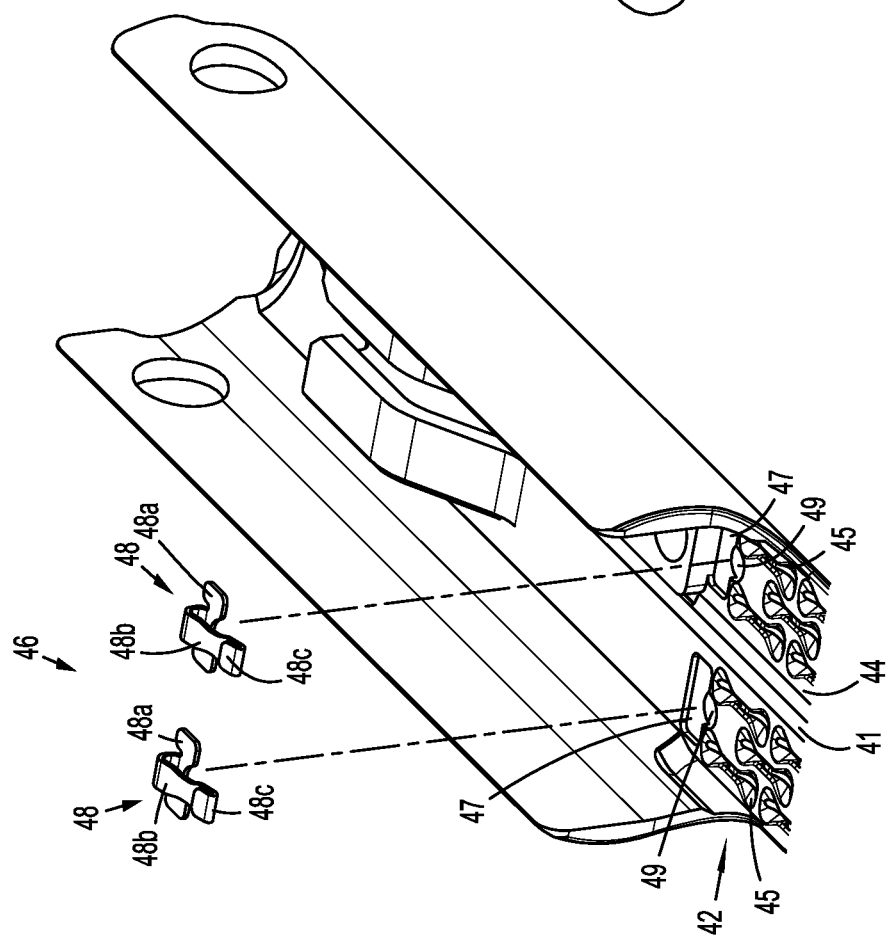
FIG. 5 is a partial, perspective view of the anvil of FIG. 3, shown with the spring assembly separated from the anvil.

As shown in FIGS. 4 and 5, the spring assembly 46 includes a pair of springs 48, with each spring 48 disposed on opposed sides of the central longitudinal slot 41. Each spring 48 includes a base 48a, an arm 48b extending distally from the base 48a, and a finger 48c disposed at a distal end of the arm 48b. The base 48a is anchored or secured (e.g., welded or otherwise attached) to the tissue facing surface 44 of the anvil body 42 proximal to the staple forming pocket 45 and, in aspects, the base 48a is retained within a recess 47 defined in the tissue facing surface 44. The arm 48b extends distally from the base 48a and overlies a through-hole 49 (FIG. 5) that extends through the outer and tissue facing surfaces 43, 44 of the anvil body 42. The finger 48c is biased against (e.g., in direct contact with) the tissue facing surface 44 of the anvil body 42 adjacent the staple forming pocket 45. The arm 48b is flexible such that the finger 48c is movable away from (e.g., capable of being raised off of) the tissue facing surface 44 of the anvil body 42 upon application of a force thereto.

Figure 6:
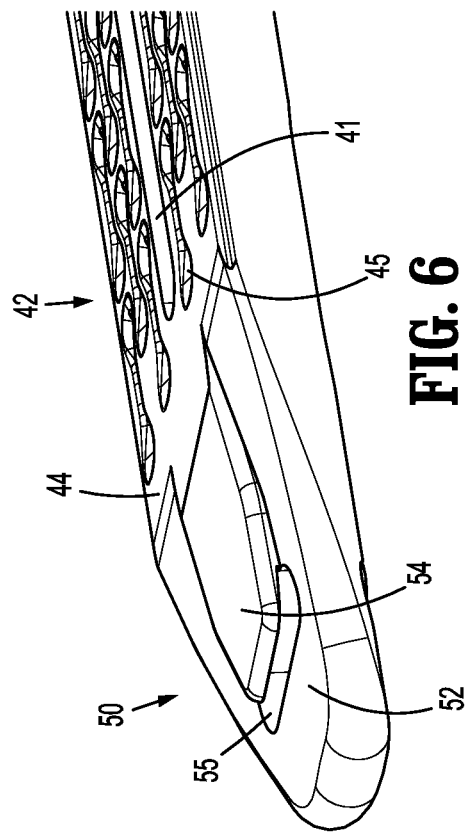
FIG. 6 is a partial, perspective view of an anvil tip of the anvil of FIG. 3.

As shown in FIG. 6, in conjunction with FIG. 3, the anvil tip 50 extends from the anvil body 42 distal to the central longitudinal slot 41 and the staple forming pockets 45. The anvil tip 50 includes an inner surface 52 contiguous with and extending distally from the tissue facing surface 44 of the anvil body 42. The inner surface 52 may be angled or taper distally from the anvil body 42. The inner surface 52 includes a hook 54 extending distally over the inner surface 52 and, in aspects, the hook 54 extends over an opening 55 defined through the anvil tip 50.

With reference again to FIG. 2, the staple cartridge assembly 60 includes a cartridge carrier 62 configured and dimensioned to selectively receive and support a staple cartridge 64 therein. A drive assembly (not shown) is supported in the anvil and staple cartridge assemblies 40, 60 and slidable relative thereto to fire staples (not shown) from the staple cartridge 64 and to cut tissue disposed between the anvil and staple cartridge assemblies 40, 60 during actuation of the surgical stapling apparatus 1 (FIG. 1).

Figure 8:
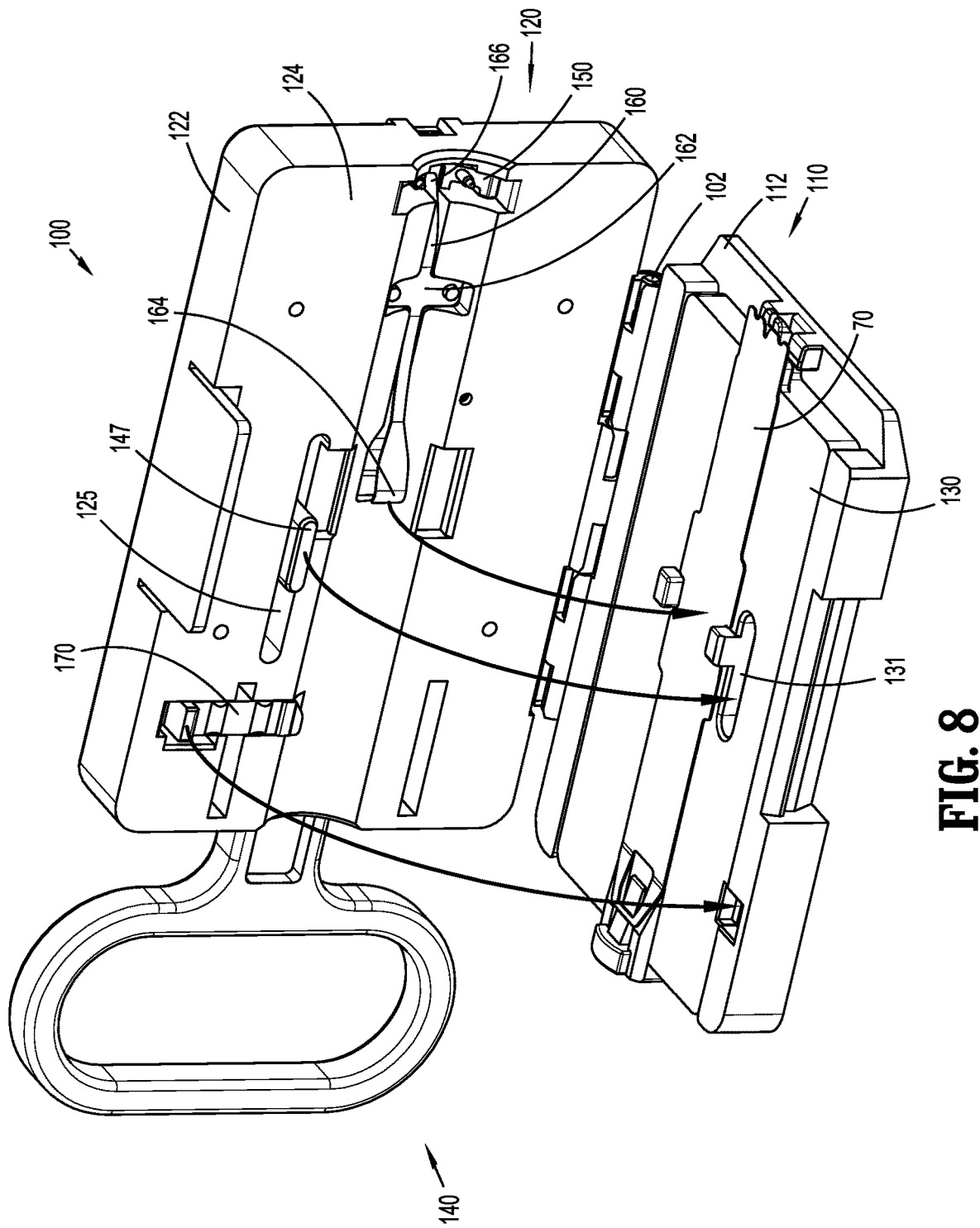
FIG. 8 is a perspective view of the loading tool of FIG. 7, shown in an open position.

Turning now to FIGS. 7 and 8, a surgical buttress loading tool 100 (also referred to herein generally as a loading tool) is shown for loading a surgical buttress 70 (FIG. 8) onto the anvil 40 (FIG. 2). The loading tool 100 includes a first housing portion 110 hingedly connected to a second housing portion 120 (e.g., about a hinge pin 102) such that the loading tool 100 is movable between a closed position (FIG. 7) and an open position (FIG. 8). In the closed position, the loading tool 100 defines a proximal opening 101 into a cavity 103 (FIG. 15) defined between the first and second housing portions 110, 120 that is sized and shaped to receive the anvil 40 (FIG. 2). In the open position, a buttress cartridge 130 may be placed into or removed from the loading tool 100.

Figure 9:
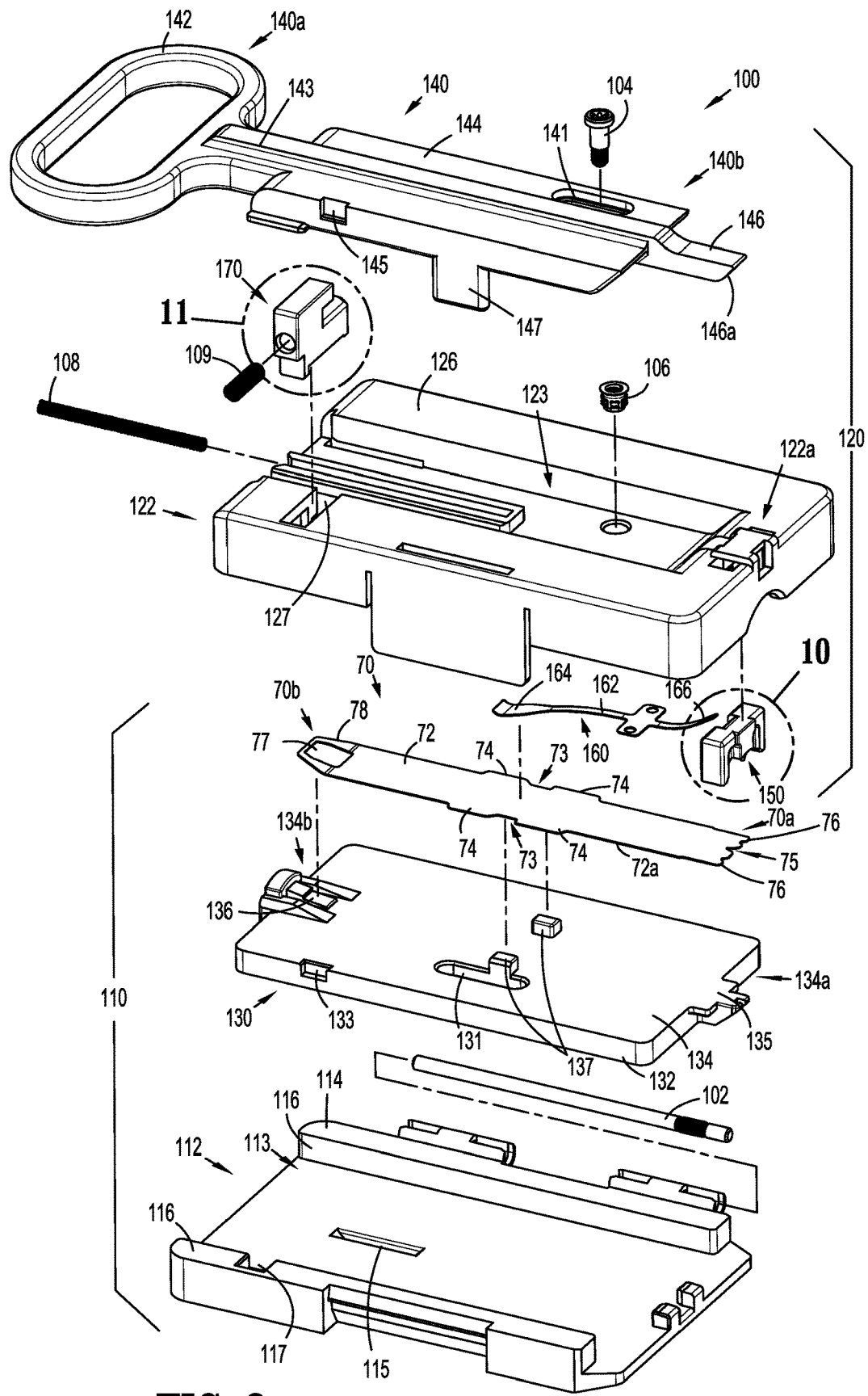
FIG. 9 is a perspective view of the loading tool of FIG. 7, shown with parts separated.

As shown in FIGS. 7-9, the first housing portion 110 includes a first housing body 112 supporting the buttress cartridge 130 and the surgical buttress 70 thereon, and the second housing portion 120 includes a second housing body 122 supporting a handle 140, an actuator 150, an applicator spring 160, and an interlock 170. The surgical buttress 70 is releasably retained on the buttress cartridge 130 which is removably positionable within the first housing portion 110 and slidable relative to the first housing body 112. The handle 140 is slidable relative to the second housing body 122 between unactuated and actuated positions, and is configured to move the actuator 150 into engagement with the spring assembly 46 (FIG. 3) of the anvil 40 when the anvil 40 is positioned within the cavity 103 (FIG. 15) of the loading tool 100 and to slide the buttress cartridge 130 towards the anvil 40 for loading the surgical buttress 70 thereon. The applicator spring 160 is configured to hold the surgical buttress 70 against the buttress cartridge 130 until the anvil 40 (FIG. 2) is positioned into the loading tool 100 and to bias the actuator 150 in a retracted position within the second housing body 122 until the handle 140 moves the actuator 150 to an extended position. The interlock 170 is configured to lock the handle 140 and the buttress cartridge 130 from movement until the anvil 40 (FIG. 2) is positioned within the loading tool 100.

As seen in FIG. 9, the surgical buttress 70 includes a buttress body 72 having a pair of tabs 74 extending laterally from each longitudinal side 72a of the buttress body 72 in spaced relation relative to each other to define a recess 73 on opposed sides of the buttress body 72. The recesses 73 are configured to engage protrusions 137 of the buttress cartridge 130 when the surgical buttress 70 is positioned on the buttress cartridge 130. A proximal end portion 70a of the surgical buttress 70 includes a v-shaped notch 75 defined therein and proximal tabs 76 disposed on opposed sides of the v-shaped notch 75. A distal end portion 70b of the surgical buttress 70 includes a window 77 defined in a distal tab 78.

The buttress cartridge 130 includes a cartridge body 132 having an inner surface 134 that faces an inner surface 124 (FIG. 8) of the second housing portion 120. The inner surface 134 is configured to support and releasably retain the surgical buttress 70 thereon. The inner surface 134 includes a proximal end portion 134a having a central bump-out 135 upon which the proximal end portion 70a of the surgical buttress 70 is placed, a distal end portion 134b including a ramped or stepped surface 136 over which the distal end portion 70b of the surgical buttress 70 is placed, and a pair of opposed and spaced protrusions 137 extending upwardly towards the second housing portion 120 between which the buttress body 72 of the surgical buttress 70 is placed. The central bump-out 135 is configured so that the proximal tabs 76 of the surgical buttress 70 do not overlie the inner surface 134 of the buttress cartridge 130, the stepped surface 136 is configured so that the distal tab 78 of the surgical buttress 70 is disposed at an angle with respect to the buttress body 72, and the protrusions 137 are shaped for positioning within the recesses 73 of the surgical buttress 70 to aid in proper alignment of the surgical buttress 70 on the buttress cartridge 130 and to minimize movement of the surgical buttress 70 relative to the buttress cartridge 130.

The buttress cartridge 130 further includes an elongated slot 131 defined through the inner surface 134 which is configured to receive a tab 147 of the handle 150 when the loading tool 100 is in the closed position, and a notch 133 defined in an outer edge thereof that is configured to engaged the interlock 170 when the loading tool 100 is in the closed position and the anvil 40 (FIG. 2) is not disposed within the loading tool 100.

The buttress cartridge 130 is removably positionable within a channel 113 of the first housing body 112 that is defined in an inner surface 114 between a pair of opposed rails 116. The buttress cartridge 130 includes a tab 138 (FIG. 12) configured for slidable receipt within an elongated slot 115 of the first housing body 112. The first housing body 112 further includes a notch 117 defined in one of the rails 116 that is aligned with the notch 133 of the buttress cartridge 130 and into which the interlock 170 is moved when the anvil 40 (FIG. 2) is positioned within the loading tool 100.

With continued reference to FIG. 9, the handle 140 includes a head 142 at a distal end 140a thereof, a neck 143 extending proximally from the head 142, a handle body 144 extending proximally from the neck 143, and a tail 146 at a proximal end 140b thereof. The head 142 extends outwardly beyond the second housing body 122 and is configured for grasping by a user. The handle body 144 is secured within a channel 123 defined in an outer surface 126 of the second housing body 122 and is longitudinally slidable relative thereto. The handle body 144 includes a longitudinally extending slot 141 defined therethrough in which a screw 104 is positioned. The screw 104 is engaged (e.g., threadingly engaged) with an insert 106 disposed within the second housing body 122 to limit longitudinal movement of the handle 140 relative to the second housing body 122. The handle body 144 further includes a notch 145 defined in a longitudinal side thereof that is configured to engage the interlock 170 when the anvil 40 (FIG. 2) is not disposed within the loading tool 100, and a tab 147 extending downwardly form the handle body 144 and through an elongate slot 125 (FIG. 8) defined through the second housing body 122. When the loading tool 100 is in the closed position, the tab 147 of the handle body 144 extends into the elongated slot 131 of the buttress cartridge 130. The tail 146 has a sloped proximal end 146a that is positioned adjacent to (e.g., against) the actuator 150 and is configured to cam the actuator 150 downwardly towards the first housing portion 110 upon movement of the handle 140 to the actuated position. The handle 140 is biased in the unactuated position (FIG. 7) by a spring 108 positioned within the second housing body 122.

Figure 10:
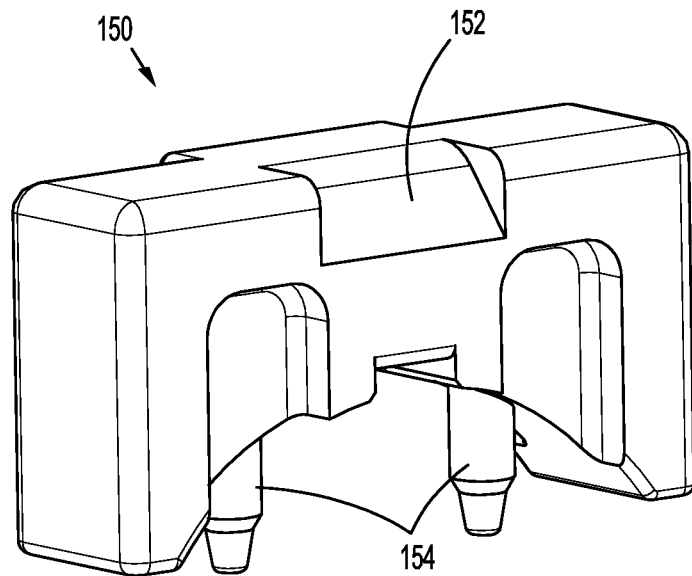
FIG. 10 is a close-up view of the area of detail 10 in FIG. 9, illustrating an actuator of the loading tool.

The actuator 150 is disposed within a proximal end portion 122a of the second housing body 122 and is movable into the cavity 103 (FIG. 15) defined between the first and second housing bodies 112, 122. As shown in FIG. 10, the actuator 150 includes a ramped surface 152 configured to engage the sloped proximal end 146a (FIG. 9) of the tail 146 of the handle 140 such that when the handle 140 is moved proximally, the tail 146 engages the actuator 150 and pushes the actuator 150 downwardly towards the first housing portion 110. The actuator 150 further includes a pair of pins 154 sized and shaped to extend through the through-holes 49 (FIG. 2) of the anvil 40 when the anvil 40 is inserted into the loading tool 100 and to contact and move the springs 48 (FIG. 4) of the spring assembly 46.

With continued reference to FIG. 9, the applicator spring 160 includes a spring body 162 secured to the inner surface 124 (FIG. 8) of the second housing portion 122. The applicator spring 160 includes a spring arm 164 extending distally from the spring body 162 that is configured to engage the surgical buttress 70 and hold the surgical buttress 70 down against the buttress cartridge 130 until the anvil 40 (FIG. 2) is positioned within the loading tool 100, and a spring leg 166 extending proximally from the spring body 162 that is configured to engage the actuator 150 between the pins 154 and bias the actuator 150 into the retracted state (FIG. 8).

Figure 11:
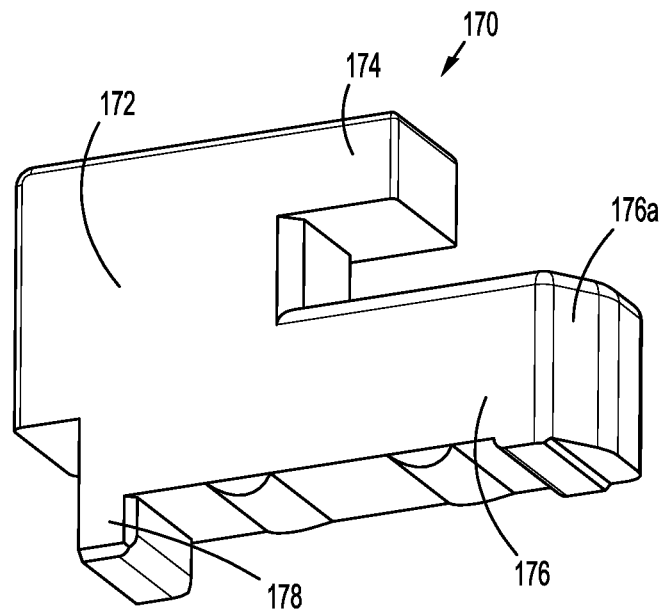
FIG. 11 is a close-up view of the area of detail 11 in FIG. 9, illustrating an interlock of the loading tool.

The interlock 170 is disposed within a laterally extending slot 127 defined in the second housing body 122 adjacent to the handle 140. As shown in FIG. 11, in conjunction with FIG. 9, the interlock 170 includes an interlock body 172 including first and second arms 174, 176 extending laterally therefrom in spaced relation relative to each other and a leg 178 extending downwardly towards the first housing portion 110. The interlock 170 is biased into a locked position by a spring 109. In the locked position, the first arm 174 is disposed within the notch 145 of the handle 140, the second arm 176 extends into the cavity 103 (FIG. 17) defined between the first and second housing portions 110, 120, and the leg 178 is disposed within the notch 133 of the buttress cartridge 130 so that the handle 140 cannot be moved. When an anvil 40 (FIG. 2) is inserted into the cavity 103 (FIG. 17), the anvil 40 cams against a beveled surface 176a (FIG. 11) of the second arm 176 of the interlock 170, pushing the interlock 170 laterally outwardly to an unlocked position so that the first arm 174 moves out of the notch 145 of the handle and the leg 178 moves out of the notch 133 of the buttress cartridge 130 and into the notch 117 of the first housing body 112, thereby releasing the handle 140.

Figure 12:
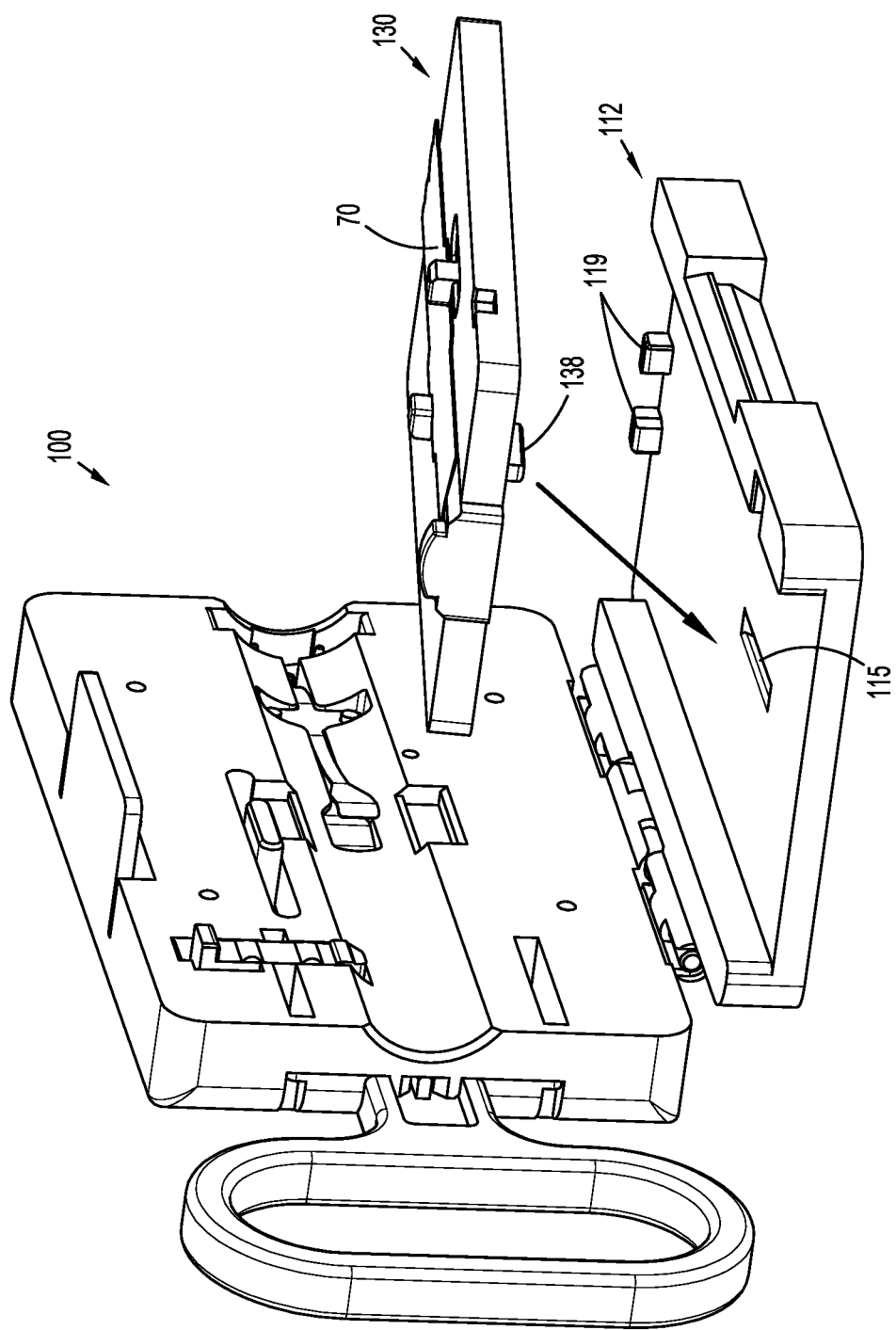
FIG. 12 is a perspective view of the loading tool of FIG. 8, shown in an open position with a buttress cartridge separated from a first housing body.

Turning now to FIG. 12, the loading tool 100 is loaded with a surgical buttress 70 by positioning a buttress cartridge 130 containing the surgical buttress 70 (e.g., the buttress cartridge may be pre-loaded with the surgical buttress by, for example, the manufacturer) within the loading tool 100. The buttress cartridge 130 is loaded by placing the tab 138 of the buttress cartridge 130 into the elongated slot 115 of the first housing portion 112 and positioning a proximal end of the buttress cartridge 130 against protrusions 119 disposed at a proximal end of the first housing body 112. It should be understood that a spent buttress cartridge 130 may be removed from the loading tool 100 and replaced with a fresh buttress cartridge 130 for re-use of the loading tool 100. Once loaded with a buttress cartridge 130 containing a surgical buttress 70, the loading tool 100 is closed for use, as shown in FIG. 13.

Figure 13:
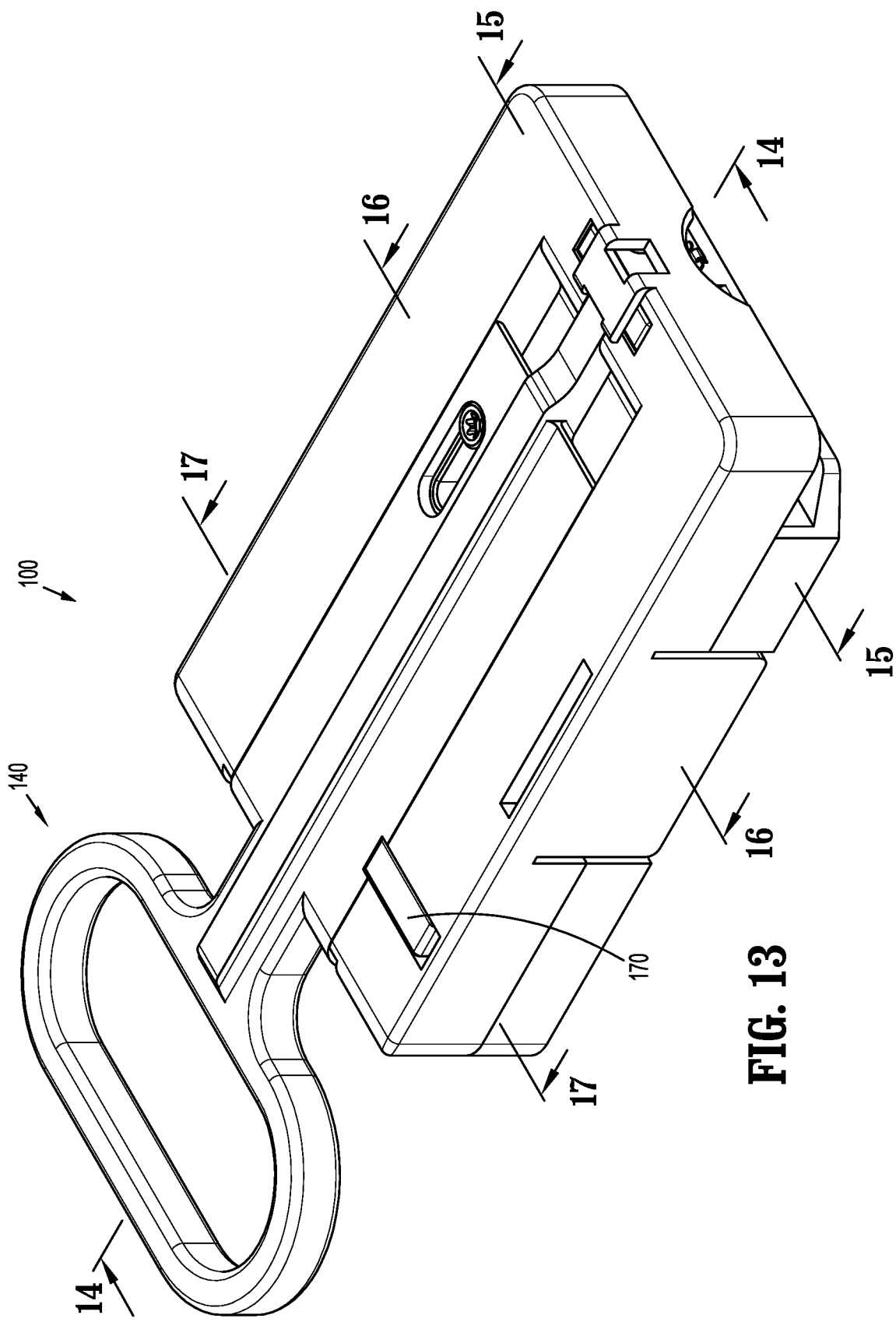
FIG. 13 is a perspective view of the loading tool of FIG. 12, shown in a closed position with a handle in an unactuated position.
Figure 14:
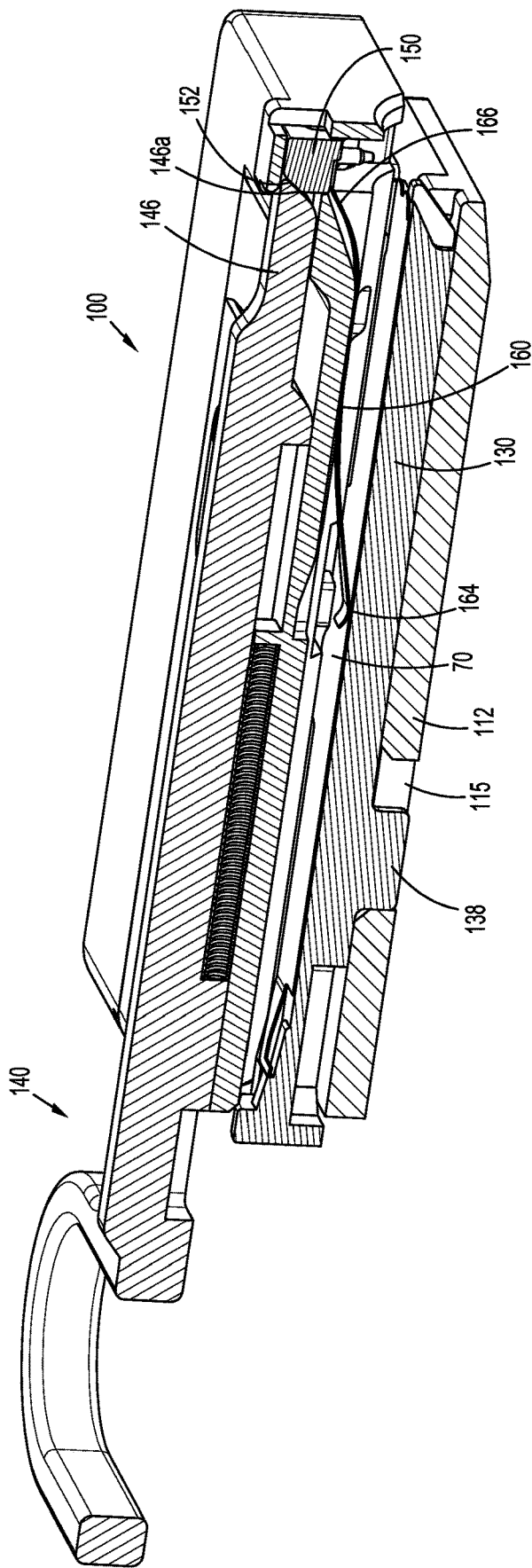
FIG. 14 is a cross-sectional view of loading tool of FIG. 13, taken along section line 14-14 of FIG. 13.
Figure 15:
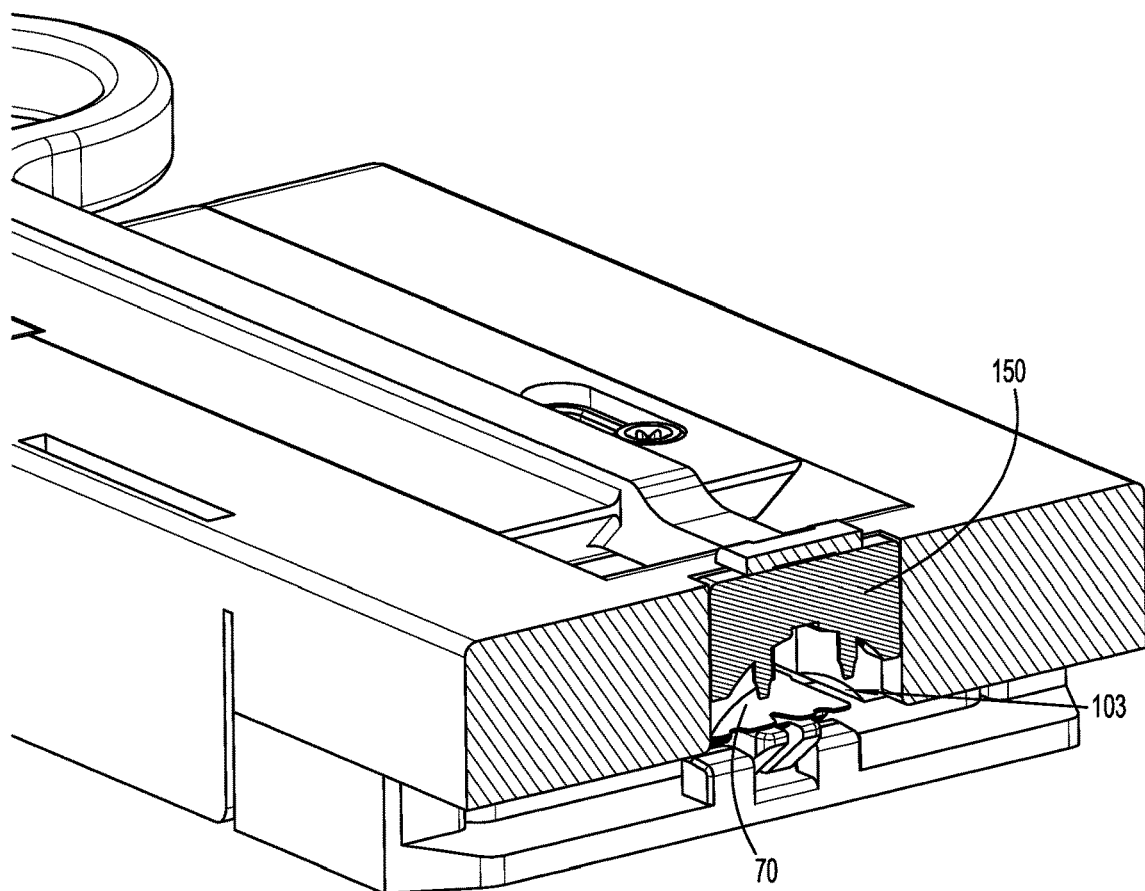
FIG. 15 is a cross-sectional view of loading tool of FIG. 13, taken along section line 15-15 of FIG. 13.
Figure 16:
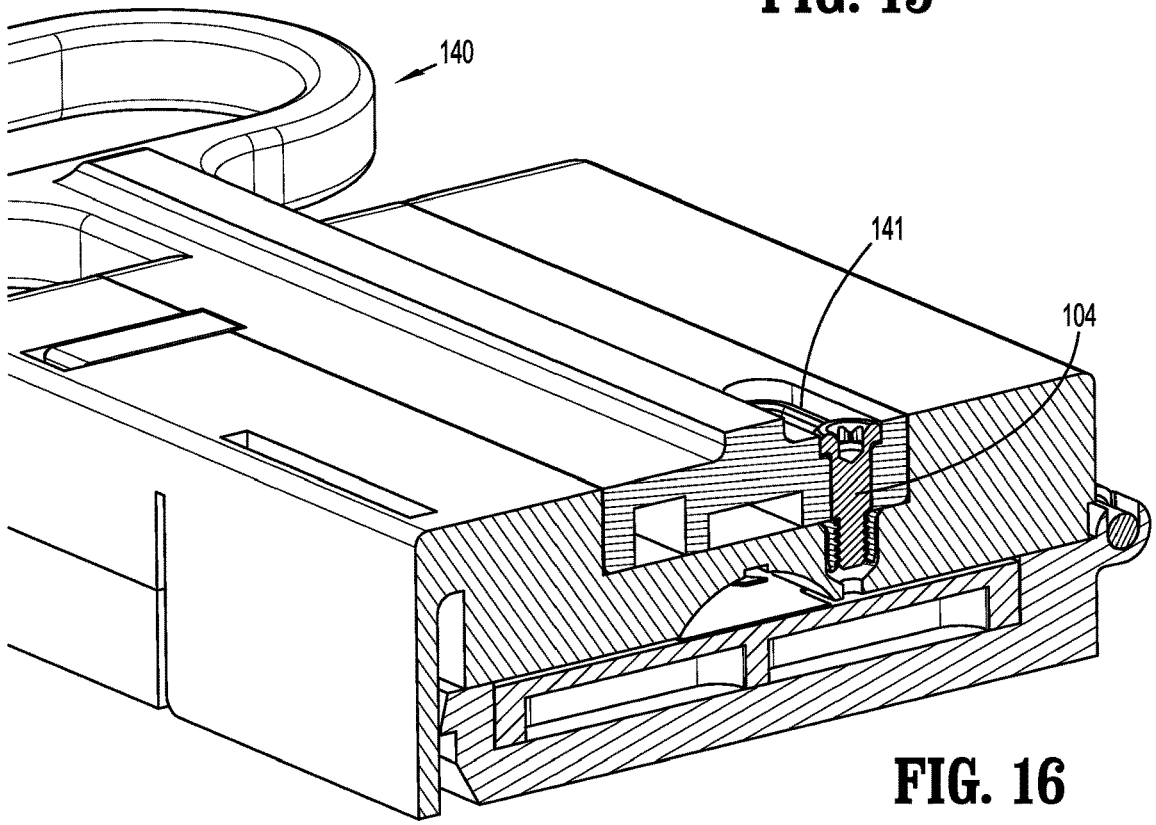
FIG. 16 is a cross-sectional view of loading tool of FIG. 13, taken along section line 16-16 of FIG. 13.

In the closed position, as shown in FIGS. 13 and 14, the tab 138 of the buttress cartridge 130 is disposed within the elongated slot 115 of the first housing body 112, as described above, and the spring arm 164 of the applicator spring 160 contacts and holds the surgical buttress 70 down against the buttress cartridge 130. Further, the spring leg 166 of the applicator spring 160 biases the actuator 150 in the retracted position, as seen in FIGS. 14 and 15, so that the actuator 150 is positioned above the cavity 103 and the surgical buttress 70 is disposed distal to the actuator 150. With continued reference to FIGS. 13 and 14, the handle 140 is disposed in the unactuated position with the sloped proximal end 146a of the tail 146 positioned adjacent to the ramped surface 152 of the actuator 150 and, as also seen in FIG. 16, the screw 104 disposed in a proximal-most portion of the longitudinally extending slot 141. As shown in FIGS. 13 and 17, the interlock 170 is in the locked state with the first arm 174 of the interlock 170 disposed within the notch 145 of the handle 140 so that the handle 140 cannot be moved distally without an anvil 40 (FIG. 2) inserted into cavity 103 as the second arm 176 of the interlock 170 extends partially into the cavity 103.

The loading tool 100 is configured to engage the anvil 40 for loading the surgical buttress 70 onto the anvil 40 (e.g., transferring the surgical buttress 70 from the loading tool 100 to the anvil 40). The anvil 40 is aligned with the proximal opening 101 of the loading tool 100 and then inserted through the proximal opening 101 and into the cavity 103 defined between the first and second housing bodies 112, 122 until the anvil 40 is fully inserted into the loading tool 100, as shown in FIG. 18. The proximal opening 101 and corresponding cavity 103 of the loading tool 100 are shaped to correspond with the shape of the anvil 40 and thus, is configured to slidably receive the anvil 40 in an orientation in which the tissue facing surface 44 of the anvil 40 faces the first housing portion 110 and the outer surface 43 faces the second housing portion 120, as seen in FIG. 20.

Figure 20:
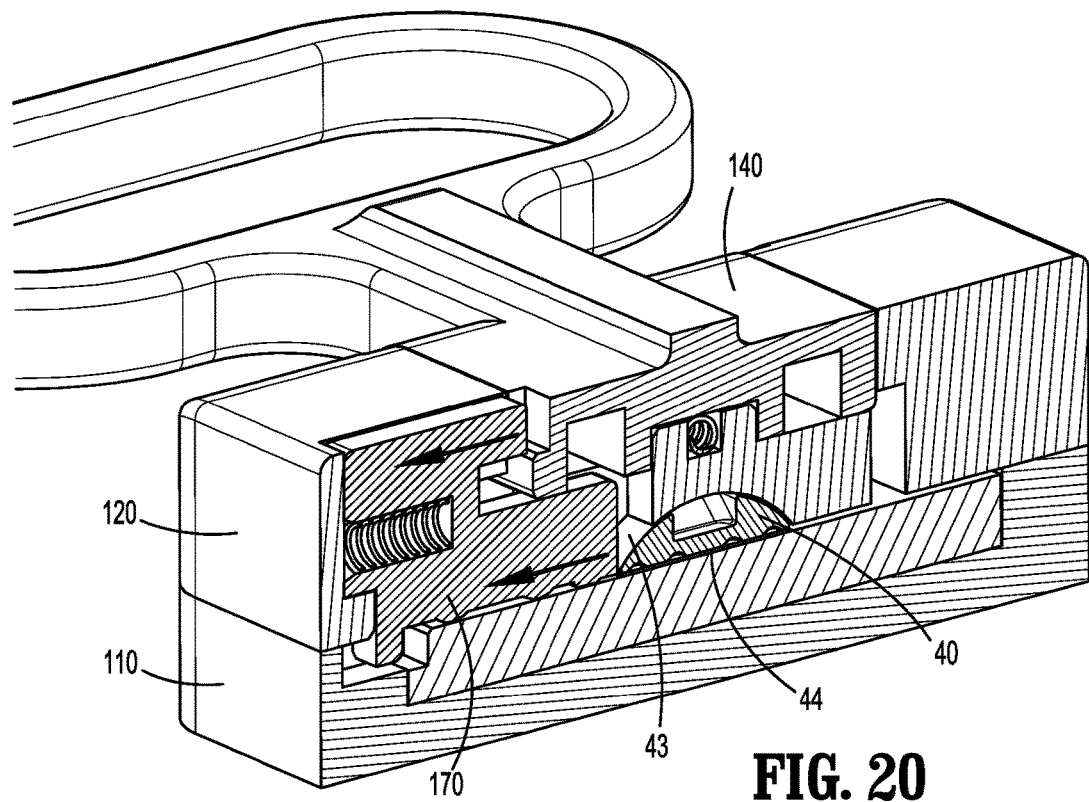
FIG. 20 is a cross-sectional view of the loading tool and the anvil of FIG. 18, taken along section line 20-20 of FIG. 18.
Figure 21:
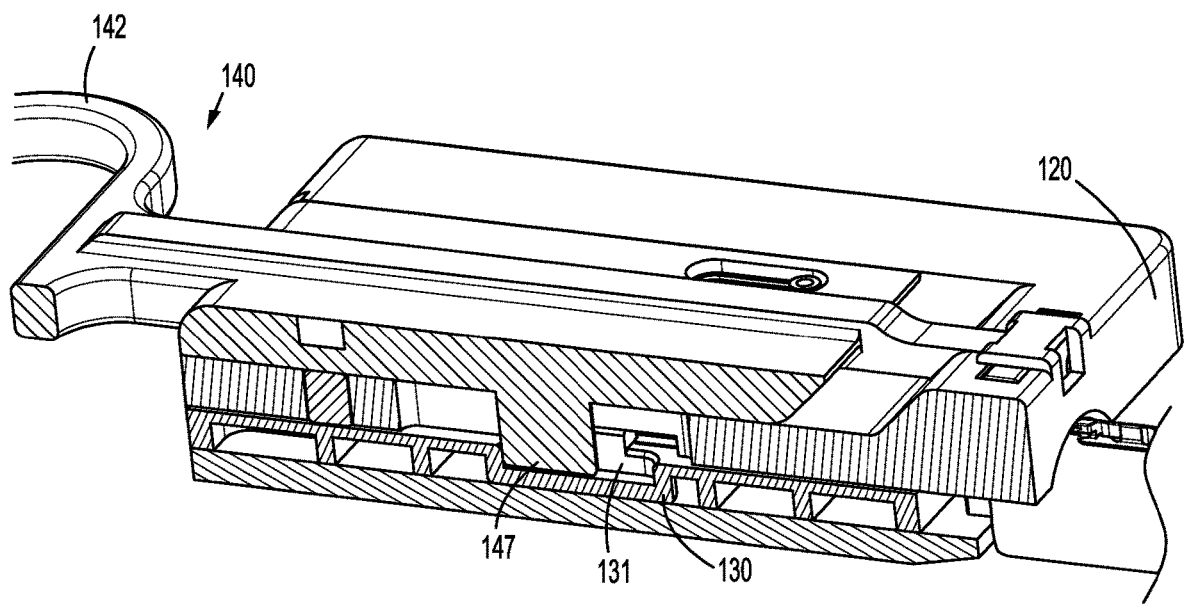
FIG. 21 is a cross-sectional view of the loading tool and the anvil of FIG. 19, taken along section line 21-21 of FIG. 19.
Figure 22:
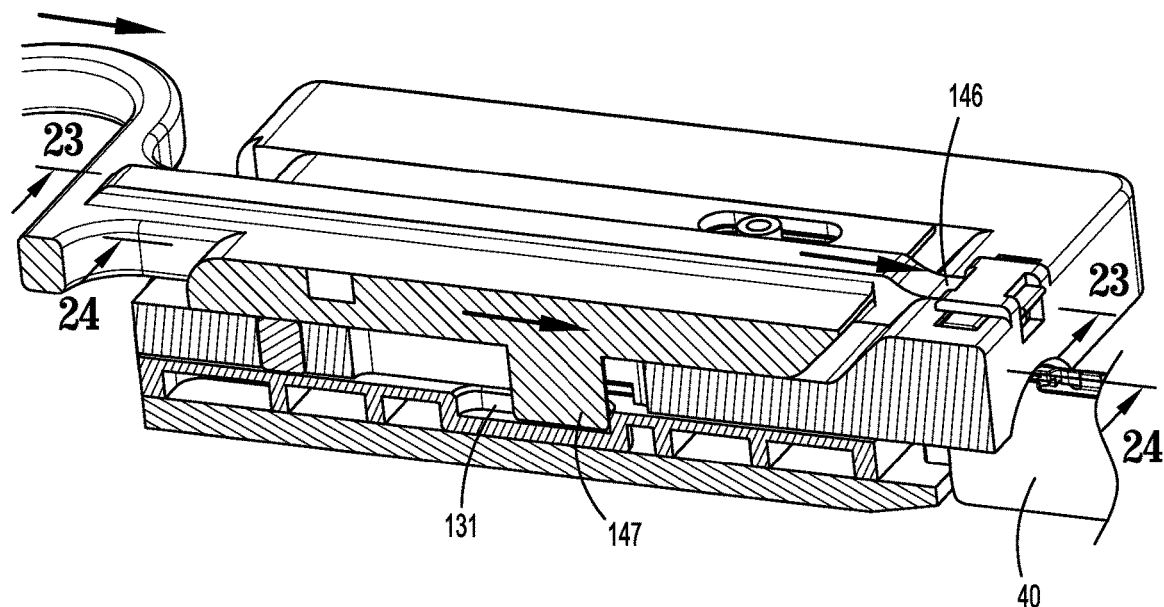
FIG. 22 is a cross-sectional view of the loading tool and the anvil of FIG. 21, during movement of the handle from the unactuated position to an actuated position.
Figure 23:
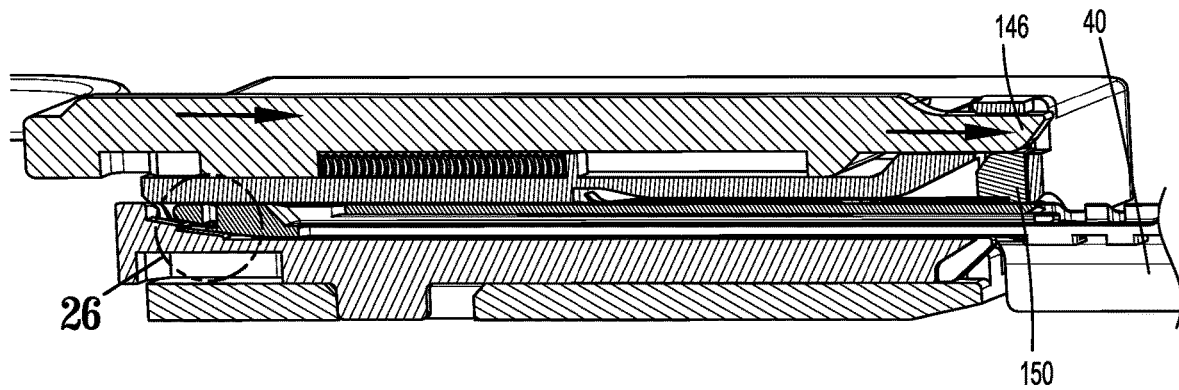
FIG. 23 is a cross-sectional view of the loading tool and the anvil of FIG. 22, taken along section line 23-23 of FIG. 22.
Figure 26:
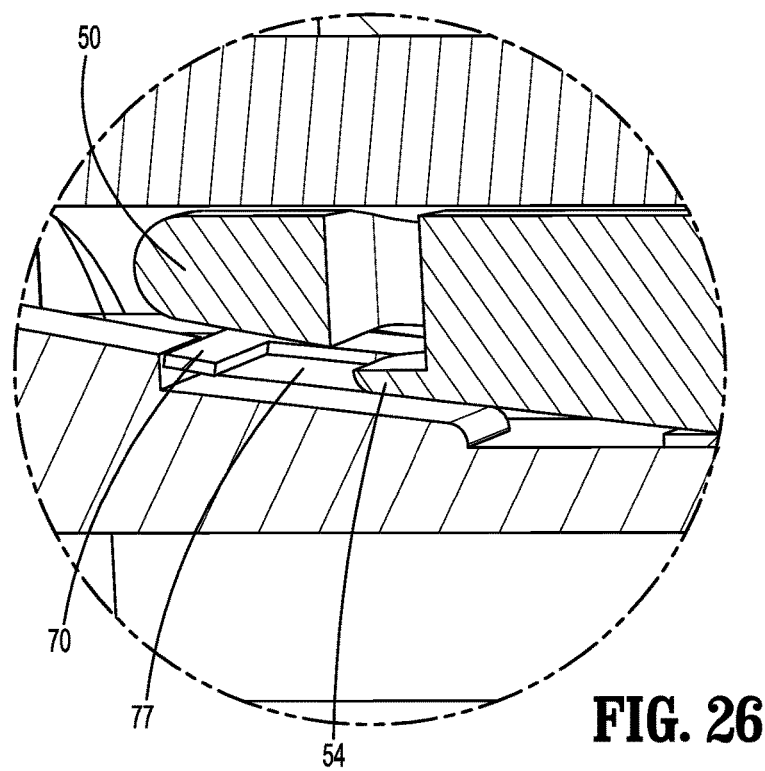
FIG. 26 is a close-up view of the area of detail 26 indicated in FIG. 23.

As shown in FIGS. 19 and 20, once the anvil 40 is fully inserted, the anvil 40 cams the interlock 170 laterally outwardly so that the handle 140 is free to move from the unactuated position to the actuated position. As shown in FIG. 21, in the unactuated position, the tab 140 of the handle 140 is initially disposed in a distal portion of the elongated slot 131 defined in the buttress cartridge 130. As the handle 140 is moved (e.g., by pushing the head 142 of the handle 140 towards or into the second housing portion 120), the tab 147 travels (e.g., slides) into a proximal portion of the elongated slot 131 before moving the buttress cartridge 130. During this initial sliding movement, with the tab 147 of the handle 140 traveling within the elongated slot 131 of the buttress cartridge 130, as seen in FIGS. 22 and 23, the tail 146 of the handle 140 cams the actuator 150 down towards the anvil 40. As shown in FIGS. 24 and 25, the pins 154 of the actuator 150, which are aligned with the through-holes 49 defined in the anvil 40, travel down through the through-holes 49 of the anvil 40 and push the springs 48 so that the fingers 48c of the springs 48 are spaced from the tissue facing surface 44 of the anvil 40. As further seen in FIG. 26, the hook 54 of the anvil tip 50 aligns with the window 77 of the surgical buttress 70.

Figure 27:
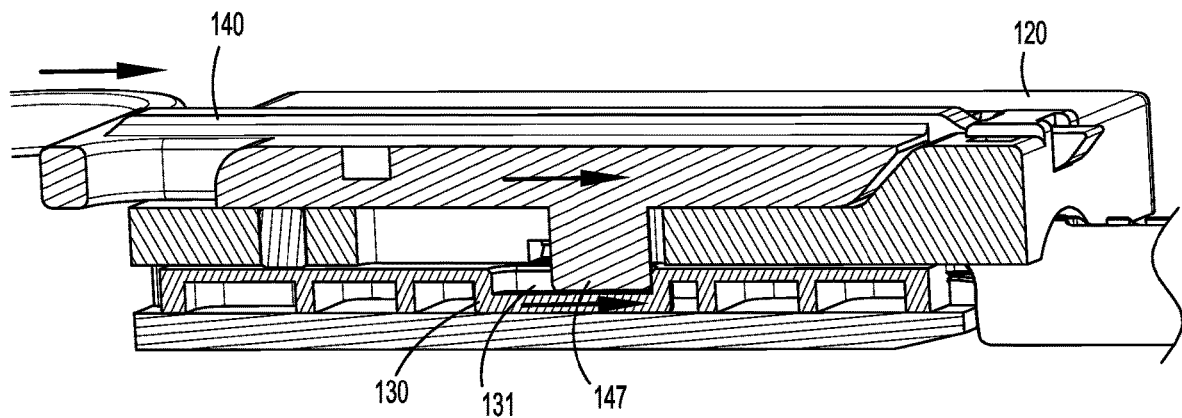
FIG. 27 is a cross-sectional view of the loading tool and the anvil of FIG. 21, shown with the handle in the actuated position.
Figure 28:
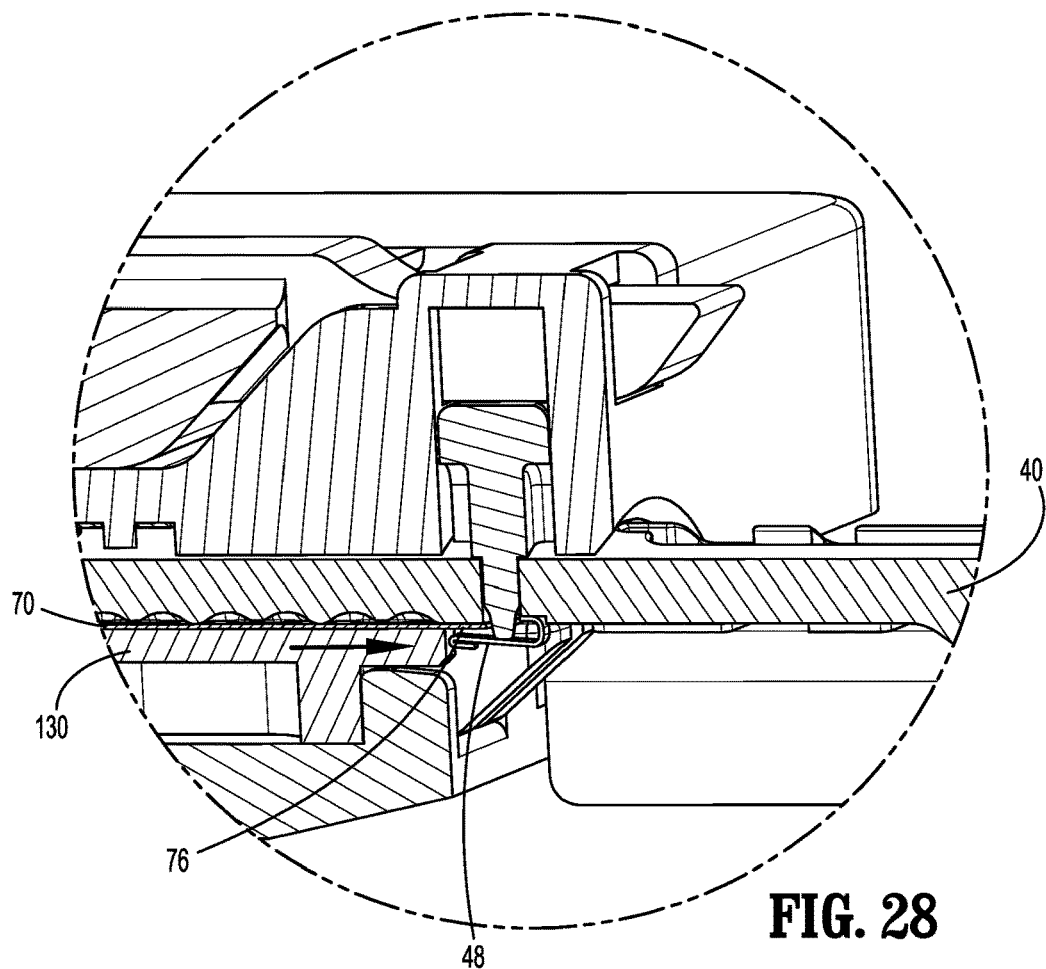
FIG. 28 is a cross-sectional view of the loading unit and anvil of FIG. 27, showing a proximal end portion of a surgical buttress engaging the anvil.
Figure 29:
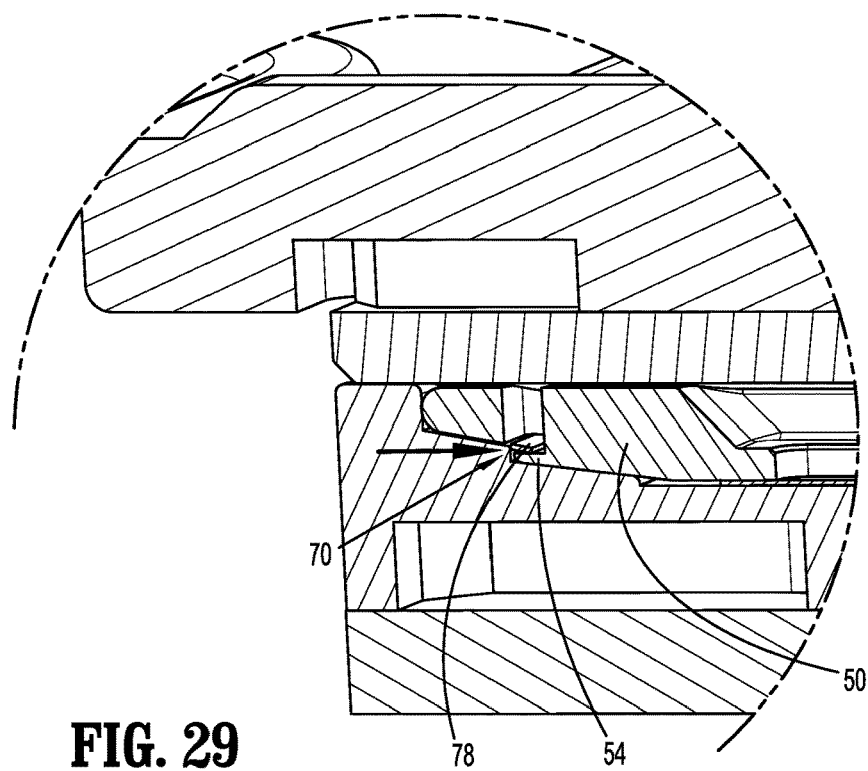
FIG. 29 is a cross-sectional view of the loading unit and anvil of FIG. 27, showing a distal end portion of the surgical buttress engaging the anvil.

Upon further movement of the handle 140 proximally into the second housing portion 120 to the actuated position, as shown in FIG. 27 (after the tab 147 of the handle 140 engages a proximal end of the elongated slot 131 of the buttress cartridge 130), the handle 140 moves the buttress cartridge 130 proximally. As the buttress cartridge 130 moves proximally, the surgical buttress 70 is also moved proximally so that the proximal tabs 76 of the surgical buttress 70 are moved under the springs 48 of the anvil 40, as shown in FIG. 28, and the distal tab 78 of the surgical buttress 70 is moved into engagement with the hook 54 of the anvil tip 50, as shown in FIG. 29.

The handle 140 may then be moved back to the unactuated position (e.g., the handle 140 may be pulled back or released so that the spring 108 drive movement distally). During this distal movement, the tail 146 of the handle 140 disengages the actuator 150 thereby freeing the actuator 150 to move back to its retracted position and out of engagement with the anvil 40, releasing the springs 48 so that the proximal tabs 76 are secured to the anvil 40. The distal tab 78 is also secured to the anvil 40 by the hook 54. Further, during this distal movement, the buttress cartridge 130 is retracted distally and away from the surgical buttress 70 which is now secured to the anvil 40. Once the handle is back in the unactuated position, the anvil 40 is removed from the loading tool 100 and the interlock 170 re-engages the handle 140 and the buttress cartridge 130.

Figure 30:
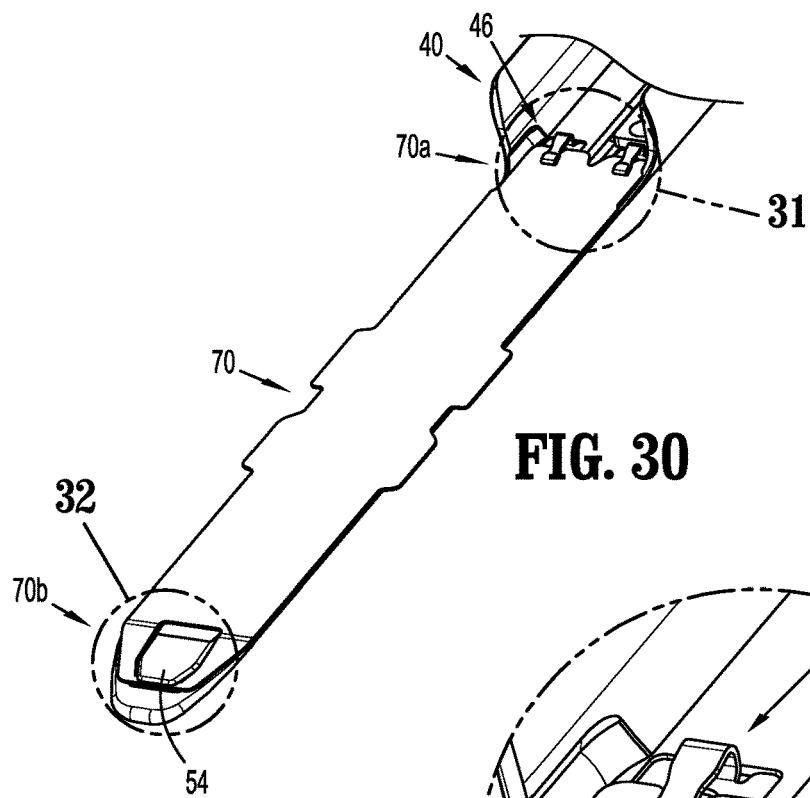
FIG. 30 is a bottom view of the surgical buttress of FIGS. 28 and 29 loaded onto the anvil.
Figure 31:
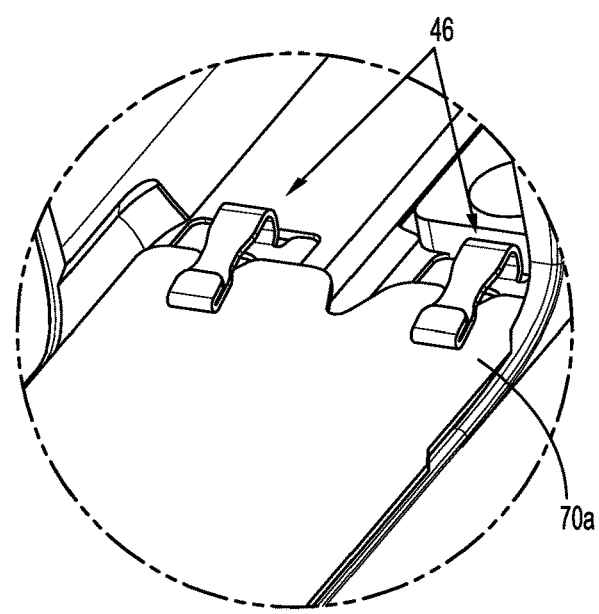
FIG. 31 is a close-up view of the area of detail 31 indicated in FIG. 30.
Figure 32:
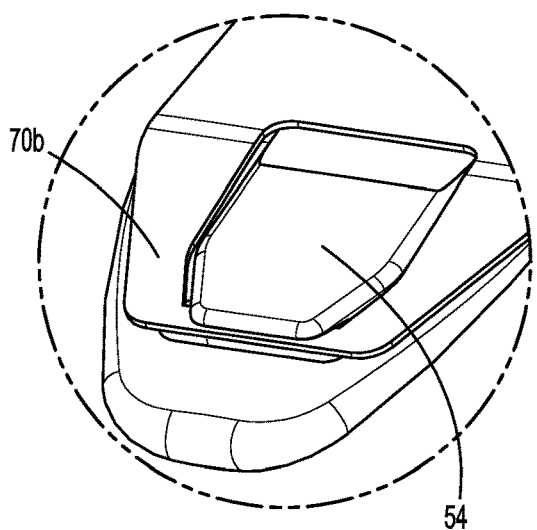
FIG. 32 is a close-up view of the area of detail 32 indicated in FIG. 30.

As shown in FIGS. 30-32, the anvil assembly 40 is loaded with the surgical buttress 70. The proximal end portion 70a of the surgical buttress 70 is retained on the anvil 40 via the spring assembly 46 and the distal end portion 70b of the surgical buttress 70 is retained on the anvil 40 via the hook 54. The surgical stapling apparatus 1 (FIG. 1), with the anvil assembly 40 loaded with the surgical buttress 70, is ready for use. In aspects, the staple cartridge assembly 60 is pre-loaded and/or loaded with a surgical buttress by any suitable attachment feature within the purview of those skilled in the art, such as, for example, mechanical attachment features (e.g., a suture), chemical attachment features (e.g., adhesive), and/or attachment methods (e.g., welding).

In operation, with the loading unit 30 loaded with the surgical buttress 70, as described above, the surgical stapling apparatus 1 is used in accordance with methods known by those skilled in the art. Once the anvil and staple cartridge assemblies 40, 60 are clamped onto tissue, the surgical stapling apparatus 1 is fired, thereby stapling the surgical buttress 70 to the tissue. During firing, a knife (not shown) travels distally through the tool assembly 34 (through the central longitudinal slot 41 of the anvil 40) and substantially simultaneously cuts and divides the tissue and the surgical buttress 70 disposed between the rows of formed staples. When firing is complete and the anvil and staple cartridge assemblies 40, 60 are unclamped, the surgical buttress 70, which is now stapled to the tissue, pulls away from the anvil 40, and the tool assembly 34 can be removed from the surgical site. The used staple cartridge 64 may then be removed from the tool assembly 34 and replaced with a new staple cartridge 64. A new surgical buttress 70 may be installed onto the anvil 40, as needed or desired, as described above.

While illustrated as being used on a handheld powered surgical device hereinabove, it is contemplated, and within the scope of the disclosure for the surgical buttress loading tools to be configured for use with handheld manually-actuated surgical devices, as well as other electrosurgical instruments. For example, the surgical buttress loading tools may be used on handheld manually actuated surgical devices, such as those shown and described in U.S. Pat. Nos. 4,473,077, 5,915,616, 5,964,394, 6,330,965, 7,128,253, and 7,334,717, the entire contents of each of which are incorporated herein by reference. As another example, the surgical buttress loading tools may be used on robotic surgical systems, such as the robotic surgical system shown and described in U.S. Pat. No. 8,828,023, the entire contents of which are incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical loading unit for a surgical device, the surgical loading unit comprising:
   an anvil including an anvil body defining a longitudinally extending knife slot and at least one longitudinally extending row of staple forming pockets disposed on each side of the knife slot, wherein each row of staple forming pockets includes a distal-most staple forming pocket and a proximal-most staple forming pocket; and
   a spring assembly disposed on each side of the knife slot, wherein each spring assembly is axially aligned with a respective row of staple forming pockets, and wherein at least a portion of each spring assembly extends distally of the proximal-most staple forming pocket.

2. The surgical loading unit according to claim 1, wherein the at least one longitudinally extending row of staple forming pockets includes:
   at least two rows of longitudinally extending rows of staple forming pockets disposed on a first side of the knife slot, wherein:
      a first row of the at least two rows of staple forming pockets disposed on the first side of the knife slot defines the proximal-most staple forming pocket;
      a second row of the at least two rows of staple forming pockets disposed on the first side of the knife slot is off-set distally of the first row of the at least two rows of staple forming pockets;

at least a portion of each spring assembly extends distally of the proximal-most staple forming pocket of the first row of the at least two rows of staple forming pockets disposed on the first side of the knife slot; and the at least a portion of each spring assembly is axially aligned proximally of the second row of the at least two rows of staple forming pockets disposed on the first side of the knife slot; and at least two rows of longitudinally extending rows of staple forming pockets disposed on a second side of the knife slot, wherein:

a first row of the at least two rows of staple forming pockets disposed on the second side of the knife slot defines the proximal-most staple forming pocket;

a second row of the at least two rows of staple forming pockets disposed on the second side of the knife slot is off-set distally of the first row of the at least two rows of staple forming pockets;

at least a portion of each spring assembly extends distally of the proximal-most staple forming pocket of the first row of the at least two rows of staple forming pockets disposed on the second side of the knife slot; and the at least a portion of each spring assembly is axially aligned proximally of the second row of the at least two rows of staple forming pockets disposed on the second side of the knife slot.

3. The surgical loading unit according to claim 1, wherein each spring assembly includes a spring having an arm extending over a through-hole defined in the anvil body.

4. The surgical loading unit according to claim 1, wherein the anvil includes an anvil tip extending distally from the anvil body, the anvil tip including a hook.

5. The surgical loading unit according to claim 1, wherein the knife slot is centrally located in the anvil body.

6. A surgical device, comprising:
the surgical loading unit according to claim 1; and
a staple cartridge assembly operatively connected to the anvil, wherein the anvil and the staple cartridge assembly are pivotally connected to one another.

7. The surgical device according to claim 6, wherein the staple cartridge assembly includes a knife slot for operative association with the knife slot of the anvil.

8. The surgical device according to claim 7, wherein the staple cartridge assembly includes a row of staple retaining pockets corresponding to each row of staple forming pockets of the anvil, and wherein each staple retaining pocket includes a staple loaded therein.

9. The surgical device according to claim 6, further comprising a surgical buttress overlying the staple forming pockets of the anvil, wherein a proximal end of the surgical buttress is captured between the anvil body and the spring assembly.

10. A surgical loading unit for a surgical device, the surgical loading unit comprising:
an anvil including:
an anvil body defining a longitudinally extending knife slot and at least one longitudinally extending row of staple forming pockets disposed on each side of the knife slot, wherein each row of staple forming pockets includes a distal-most staple forming pocket and a proximal-most staple forming pocket; and
a spring assembly disposed on each side of the knife slot, wherein each spring assembly is axially aligned with a respective row of staple forming pockets, and wherein at least a portion of each spring assembly extends distally of the proximal-most staple forming pocket;

a staple cartridge assembly operatively connected to the anvil, wherein the anvil and the staple cartridge assembly are pivotally connected to one another; and a surgical buttress overlying the staple forming pockets of the anvil, wherein a proximal end of the surgical buttress is captured between the anvil body and the spring assembly.

11. The surgical loading unit according to claim 10, wherein the at least one longitudinally extending row of staple forming pockets of the anvil includes:

at least two rows of longitudinally extending rows of staple forming pockets disposed on a first side of the knife slot, wherein:

a first row of the at least two rows of staple forming pockets disposed on the first side of the knife slot defines the proximal-most staple forming pocket;

a second row of the at least two rows of staple forming pockets disposed on the first side of the knife slot is off-set distally of the first row of the at least two rows of staple forming pockets;

at least a portion of each spring assembly extends distally of the proximal-most staple forming pocket of the first row of the at least two rows of staple forming pockets disposed on the first side of the knife slot; and the at least a portion of each spring assembly is axially aligned proximally of the second row of the at least two rows of staple forming pockets disposed on the first side of the knife slot; and at least two rows of longitudinally extending rows of staple forming pockets disposed on a second side of the knife slot, wherein:

a first row of the at least two rows of staple forming pockets disposed on the second side of the knife slot defines the proximal-most staple forming pocket;

a second row of the at least two rows of staple forming pockets disposed on the second side of the knife slot is off-set distally of the first row of the at least two rows of staple forming pockets;

at least a portion of each spring assembly extends distally of the proximal-most staple forming pocket of the first row of the at least two rows of staple forming pockets disposed on the second side of the knife slot; and the at least a portion of each spring assembly is axially aligned proximally of the second row of the at least two rows of staple forming pockets disposed on the second side of the knife slot.

12. The surgical loading unit according to claim 10, wherein each spring assembly includes a spring having an arm extending over a through-hole defined in the anvil body.

13. The surgical loading unit according to claim 10, wherein the anvil includes an anvil tip extending distally from the anvil body, the anvil tip including a hook.

14. The surgical loading unit according to claim 10, wherein the knife slot is centrally located in the anvil body.

15. A surgical device, comprising:
the surgical loading unit according to claim 10; and
a staple cartridge assembly operatively connected to the anvil, wherein the anvil and the staple cartridge assembly are pivotally connected to one another.

16. The surgical device according to claim 15, wherein the staple cartridge assembly includes a knife slot for operative association with the knife slot of the anvil.

17. The surgical device according to claim 16, wherein the staple cartridge assembly includes a row of staple retaining pockets corresponding to each row of staple forming pockets of the anvil, and wherein each staple retaining pocket includes a staple loaded therein.

\* \* \* \* \*